(12) United States Patent
Walter et al.

(10) Patent No.: US 8,357,634 B2
(45) Date of Patent: Jan. 22, 2013

(54) N-ALKOXYCARBOXAMIDES AND THEIR USE AS MICROBIOCIDES

(75) Inventors: Harald Walter, Stein (CH); Ramya Rajan, Goa (IN); Daniel Stierli, Stein (CH)

(73) Assignee: Syngenta Crop Protection LLC, Greensboro, NC (US)

( * ) Notice: Subject to any disclaimer, the term of this patent is extended or adjusted under 35 U.S.C. 154(b) by 0 days.

(21) Appl. No.: 13/392,306

(22) PCT Filed: Aug. 23, 2010

(86) PCT No.: PCT/EP2010/062206
§ 371 (c)(1),
(2), (4) Date: Feb. 24, 2012

(87) PCT Pub. No.: WO2011/023645
PCT Pub. Date: Mar. 3, 2011

(65) Prior Publication Data
US 2012/0172407 A1    Jul. 5, 2012

(30) Foreign Application Priority Data
Aug. 25, 2009  (IN) ............................ 1760/DEL/2009

(51) Int. Cl.
*A01N 43/56*  (2006.01)
*C07D 231/10* (2006.01)

(52) U.S. Cl. ...................................... 504/280; 548/374.1
(58) Field of Classification Search .................. 504/280; 548/374.1

See application file for complete search history.

(56) References Cited

FOREIGN PATENT DOCUMENTS

| | | |
|---|---|---|
| CH | 01/09104 | 2/2001 |
| DE | 34 15 138 | 10/1985 |
| DE | 102 39 905 | 3/2004 |
| WO | 2007/087906 | 7/2007 |
| WO | 2008/148570 | 12/2008 |
| WO | 2009/024342 | 2/2009 |

*Primary Examiner* — Rebecca Anderson
*Assistant Examiner* — Samantha Shterengarts
(74) *Attorney, Agent, or Firm* — R. Kody Jones

(57) ABSTRACT

Compounds of formula (I) in which the substituents are as defined in claim 1, are suitable for use as microbiocides.

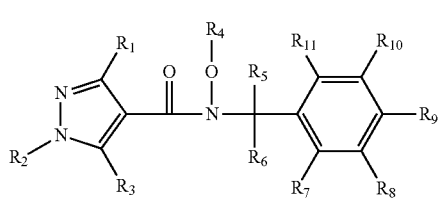

8 Claims, No Drawings

N-ALKOXYCARBOXAMIDES AND THEIR USE AS MICROBIOCIDES

This application is a 371 of International Application No. PCT/EP2010/062206 filed Aug. 23, 2010, which claims priority to 1760/DEL/2009 filed Aug. 25, 2009, the contents of which are incorporated herein by reference.

The present invention relates to novel microbiocidally active, in particular fungicidally active, carboxamides. It further relates to intermediates used in the preparation of these compounds, to compositions which comprise these compounds and to their use in agriculture or horticulture for controlling or preventing infestation of plants by phytopathogenic microorganisms, preferably fungi.

Fungicidally active carboxamides are described in WO 2007/087906 and WO 2009/024342.

It has been found that novel carboxamides with a specific substitution pattern have microbiocidal activity.

The present invention accordingly relates to N-alkoxycarboxamides of formula I

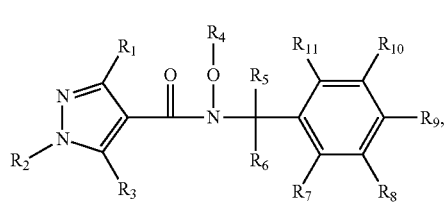

wherein
$R_1$ is $C_1$-$C_4$alkyl or $C_1$-$C_4$haloalkyl;
$R_2$ is $C_1$-$C_4$alkyl;
$R_3$ is hydrogen or halogen;
$R_4$ is hydrogen, $C_1$-$C_4$alkyl or $C_1$-$C_4$halogenalkyl;
$R_5$ and $R_6$ are, independently from each other, hydrogen, halogen, $C_1$-$C_4$alkyl or $C_1$-$C_4$haloalkyl;
$R_8$ and $R_{10}$ are, independently from each other, hydrogen, halogen, $C_1$-$C_6$alkyl, phenyl which can be mono- or di-substituted by halogen or phenoxy which can be mono- or di-substituted by halogen;
or $R_7$ and $R_8$ together or $R_8$ and $R_9$ together form together with the carbon atoms to which they are attached, a six-membered aromatic ring; and
$R_7$, $R_9$ and $R_{11}$ are, independently from each other, hydrogen, hydroxy, halogen, $C_1$-$C_6$alkyl, $C_3$-$C_6$alkinyl, $C_1$-$C_4$alkoxy, halophenoxy, $C_1$-$C_6$haloalkyl or $C_1$-$C_6$haloalkoxy;
and agronomically acceptable salts/isomers/structural isomers/stereoisomers/diastereoisomers/enantiomers/tautomers and N-oxides of those compounds.

The alkyl groups occurring in the definitions of the substituents can be straight-chain or branched and are, for example, methyl, ethyl, n-propyl, n-butyl, n-pentyl, n-hexyl, iso-propyl, n-butyl, sec-butyl, iso-butyl or tert-butyl. Alkoxy, alkenyl and alkynyl radicals are derived from the alkyl radicals mentioned. The alkenyl and alkynyl groups can be mono- or di-unsaturated. The cycloalkyl groups occuring in the definitions of the substituents are, for example, cyclopropyl, cyclobutyl, cyclopentyl or cyclohexyl. Halogen is generally fluorine, chlorine, bromine or iodine, preferably fluorine, bromine or chlorine. This also applies, correspondingly, to halogen in combination with other meanings, such as halogenalkyl or halogenalkoxy. Haloalkyl groups preferably have a chain length of from 1 to 4 carbon atoms. Halonalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl; preferably trichloromethyl, difluorochloromethyl, difluoromethyl, trifluoromethyl and dichlorofluoromethyl. Alkoxy is, for example, methoxy, ethoxy, propoxy, i-propoxy, n-butoxy, isobutoxy, sec-butoxy and tert-butoxy; preferably methoxy and ethoxy. Halogenalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy and 2,2,2-trichloroethoxy; preferably difluoromethoxy, 2-chloroethoxy and trifluoromethoxy.

In a preferred group of compounds of formula I,
$R_1$ is $C_1$-$C_4$haloalkyl;
$R_2$ is $C_1$-$C_4$ alkyl;
$R_3$ is hydrogen;
$R_4$ is $C_1$-$C_4$alkyl;
$R_5$ is hydrogen or $C_1$-$C_4$alkyl;
$R_6$ is hydrogen;
$R_7$ is hydrogen, $C_1$-$C_4$alkoxy or halogen;
$R_8$ is hydrogen, halogen, phenyl which can be mono- or di-substituted by halogen or phenoxy which can be mono- or di-substituted by halogen;
or $R_7$ and $R_8$ together or $R_8$ and $R_9$ together form together with the carbon atoms to which they are attached, a six-membered aromatic ring;
$R_9$ is hydrogen, halogen or phenoxy which can be substituted by halogen;
$R_{10}$ is hydrogen and
$R_{11}$ is hydrogen.

In preferred compound from this group, $R_5$ is methyl.

In an especially preferred group of compounds of formula I,
$R_1$ is difluoromethyl;
$R_2$ is methyl;
$R_3$ is hydrogen;
$R_4$ is methyl;
$R_5$ is hydrogen or methyl;
$R_6$ is hydrogen;
$R_7$ is hydrogen, methoxy or chlorine;
$R_8$ is hydrogen; iodine, phenyl, which is mono- or di-substituted by chlorine or phenoxy which is mono- or di-substituted by chlorine;
or $R_7$ and $R_8$ together or $R_8$ and $R_9$ together form together with the carbon atoms to which they are attached, a six-membered aromatic ring;
$R_9$ is hydrogen, iodine, chlorine or phenoxy which is substituted by chlorine;
$R_{10}$ is hydrogen and
$R_{11}$ is hydrogen.

In further preferred compounds of formula I, independently from each other,
a) $R_1$ is difluoromethyl, trifluoromethyl or methyl,
b) $R_2$ is methyl;
c) $R_3$ is hydrogen or fluoro;
d) $R_4$ is hydrogen, methyl or ethyl; preferably methyl;
e) $R_5$ is hydrogen, methyl or ethyl;
g) $R_6$ is hydrogen;
Especially preferred compounds of formula I are those, wherein
$R_1$ is difluoromethyl or trifluoromethyl;
$R_2$ is methyl;
$R_3$ is hydrogen;
$R_4$ is methyl;
$R_5$ is hydrogen, methyl or ethyl;

$R_6$ is hydrogen;

$R_8$ is hydrogen; iodine, phenyl which can be mono- or di-substituted by chlorine, phenoxy which can be mono- or di-substituted by chlorine, phenyl which can be mono- or di-substituted by chlorine, $R_{10}$ is hydrogen;

$R_7$, $R_9$ and $R_{11}$ are, independently from each other, hydrogen or halogen, preferably hydrogen or chlorine.

In a further preferred group of compounds of formula I, $R_4$ is methyl; $R_5$ is hydrogen, methyl or fluoromethyl; $R_6$ is hydrogen; $R_7$ is hydrogen, chlorine or methoxy; $R_8$ is hydrogen, iodine, 4-Cl-phenyl, 3,4-Cl$_2$-phenyl or 4-Cl-phenoxy; $R_9$ is hydrogen, chlorine, t-butyl or 4-Cl-phenoxy; or $R_7$ and $R_8$ or $R_8$ and $R_9$ form together with the carbon atoms to which they are attached, a six-membered aromatic ring; $R_{10}$ is hydrogen; and $R_{11}$ is hydrogen or chlorine.

Compounds of formula I may be prepared by reacting a compound of formula II

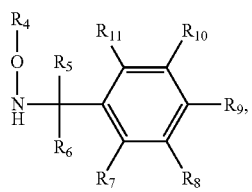

wherein $R_4$, $R_5$, $R_6$, $R_7$, $R_8$, $R_9$, $R_{10}$, and $R_{11}$ are as defined under formula I; with a compound of formula III

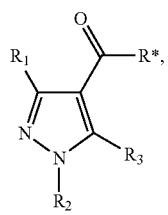

in which $R_1$, $R_2$ and $R_3$ are as defined under formula I, and R* is halogen, hydroxy or $C_{1-6}$ alkoxy, preferably chlorine.

The reactions to give compounds of formula I are advantageously carried out in aprotic inert organic solvents. Such solvents are hydrocarbons such as benzene, toluene, xylene or cyclohexane, chlorinated hydrocarbons such as dichloromethane, trichloromethane, tetrachloromethane or chlorobenzene, ethers such as diethyl ether, ethylene glycol dimethyl ether, diethylene glycol dimethyl ether, tetrahydrofuran or dioxane, nitriles such as acetonitrile or propionitrile, amides such as N,N-dimethylformamide, diethylformamide or N-methylpyrrolidinone. The reaction temperatures are advantageously between −20° C. and +120° C. In general, the reactions are slightly exothermic and, as a rule, they can be carried out at ambient temperature. To shorten the reaction time, or else to start the reaction, the mixture may be heated briefly to the boiling point of the reaction mixture. The reaction times can also be shortened by adding a few drops of base as reaction catalyst. Suitable bases are, in particular, tertiary amines such as trimethylamine, triethylamine, quinuclidine, 1,4-diazabicyclo[2.2.2]octane, 1,5-diazabicyclo[4.3.0]non-5-ene or 1,5-diazabicyclo-[5.4.0]undec-7-ene. However, inorganic bases such as hydrides, e.g. sodium hydride or calcium hydride, hydroxides, e.g. sodium hydroxide or potassium hydroxide, carbonates such as sodium carbonate and potassium carbonate, or hydrogen carbonates such as potassium hydrogen carbonate and sodium hydrogen carbonate may also be used as bases. The bases can be used as such or else with catalytic amounts of a phase-transfer catalyst, for example a crown ether, in particular 18-crown-6, or a tetraalkylammonium salt.

When R* is hydroxy, a coupling agent, such as benzotriazol-1-yloxytris(dimethylamino) phosphoniumhexafluorophosphate, bis-(2-oxo-3-oxazolidinyl)-phosphinic acid chloride (BOP-Cl), N,N'-dicyclohexylcarbodiimide (DCC) or 1,1'-carbonyl-diimidazole (CD), may be used.

The intermediates of the formula II

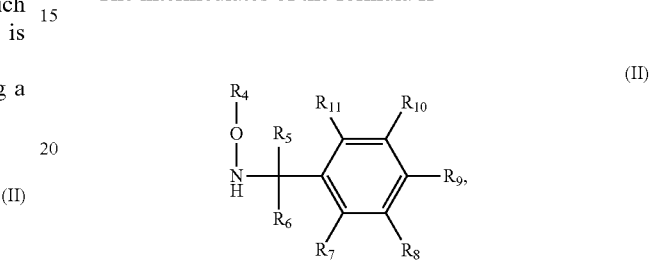

wherein $R_4$, $R_5$, $R_6$, $R_7$, $R_8$, $R_9$, $R_{10}$, and $R_{11}$ are as defined under formula I, preferably wherein $R_4$ is $C_1$-$C_4$alkyl; are novel and were developed specifically for the preparation of the compounds of the formula I. Accordingly, these intermediates of the formula II also form a part of the subject-matter of the present invention.

The preferred substituent definitions for the compounds of formula I are also valid for the compound of formula II. Thus, preferred compounds of formula II are those, wherein, $R_4$ is $C_1$-$C_4$alkyl;

$R_5$ is hydrogen or $C_1$-$C_4$alkyl;

$R_6$ is hydrogen;

$R_7$ is hydrogen or halogen;

$R_8$ is hydrogen, halogen, phenyl which can be mono- or di-substituted by halogen or phenoxy which can be mono- or di-substituted by halogen;

$R_9$ is hydrogen, halogen or phenoxy which can be substituted by halogen;

$R_{10}$ is hydrogen and $R_{11}$ is hydrogen.

In preferred compound from this group, $R_5$ is methyl.

In an especially preferred group of compounds of formula II, $R_4$ is methyl;

$R_5$ is hydrogen or methyl;

$R_6$ is hydrogen;

$R_7$ is hydrogen or chlorine;

$R_8$ is hydrogen; iodine, phenyl is mono- or di-substituted by chlorine or phenoxy which is mono- or di-substituted by chlorine;

$R_9$ is hydrogen, iodine, chlorine or phenoxy which is substituted by chlorine;

$R_{10}$ is hydrogen and $R_{11}$ is hydrogen.

In further preferred compounds of formula II, independently from each other, a) $R_4$ is hydrogen, methyl or ethyl; preferably methyl;

b) $R_5$ is hydrogen, methyl or ethyl;

c) $R_6$ is hydrogen;

Especially preferred compounds of formula II are those, wherein $R_4$ is methyl;

$R_5$ is hydrogen, methyl or ethyl;

$R_6$ is hydrogen;

$R_8$ is hydrogen; iodine, phenyl which can be mono- or di-substituted by chlorine, phenoxy which can be mono- or di-substituted by chlorine, phenyl which can be mono- or di-substituted by chlorine, $R_{10}$ is hydrogen;

$R_7$, $R_9$ and $R_{11}$ are, independently from each other, hydrogen or halogen, preferably hydrogen or chlorine.

In a further preferred group of compounds of formula II, $R_4$ is methyl; $R_5$ is hydrogen, methyl or fluoromethyl; $R_6$ is hydrogen; $R_7$ is hydrogen, chlorine or methoxy; $R_8$ is hydrogen, iodine, 4-Cl-phenyl, 3,4-Cl$_2$-phenyl or 4-Cl-phenoxy; $R_9$ is hydrogen, chlorine, t-butyl or 4-Cl-phenoxy; or $R_7$ and $R_8$ or $R_8$ and $R_9$ form together with the carbon atoms to which they are attached, a six-membered aromatic ring; $R_{10}$ is hydrogen; and $R_{11}$ is hydrogen or chlorine.

Intermediates of formula IIA

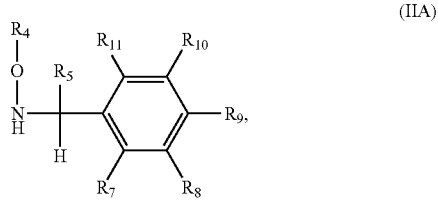

(IIA)

wherein $R_4$, $R_5$, $R_7$, $R_8$, $R_9$, $R_{10}$ and $R_{11}$ are as defined under formula I may be prepared as described in reaction scheme 1.

Scheme 1:

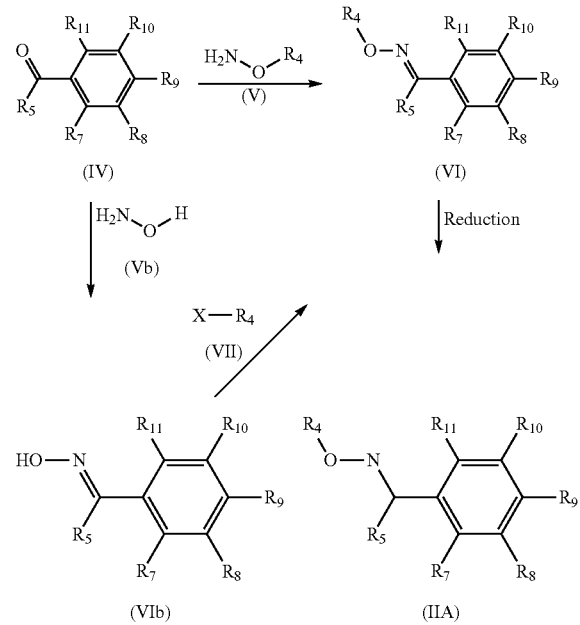

Oxime ether derivatives of formula VI, in which and $R_4$, $R_5$, $R_7$, $R_8$, $R_9$, $R_{10}$ and $R_{11}$ are as defined under formula I may be prepared by oximation of ketones or aldehydes of formula IV with O-alkyl hydroxylamine derivatives of formula V or a salt thereof. Suitable solvents carrying out the oximation step are hydrocarbons such as benzene, toluene, xylene or cyclohexane, chlorinated hydrocarbons such as dichloromethane, trichloromethane, tetrachloromethane or chlorobenzene, ethers such as diethyl ether, ethylene glycol dimethyl ether, diethylene glycol dimethyl ether, tetrahydrofuran or dioxane, nitriles such as acetonitrile or propionitrile, amides such as N,N-dimethylformamide, diethylformamide, N-methylpyrrolidinone water or mixtures. The reaction temperatures are advantageously between −20° C. and +120° C. In general, the reactions can be carried out at ambient temperature. Suitable bases are, in particular pyridine, tertiary amines such as trimethylamine, triethylamine, huenig base, quinuclidine, 1,4-diazabicyclo[2.2.2]octane, 1,5-diazabicyclo[4.3.0]non-5-ene or 1,5-diazabicyclo[5.4.0]undec-7-ene. However, inorganic bases such as hydroxides, e.g. sodium hydroxide or potassium hydroxide, carbonates such as sodium carbonate and potassium carbonate, or hydrogen carbonates such as potassium hydrogen carbonate and sodium hydrogen carbonate may also be used as bases. Alternatively, oxime ether derivatives of formula VI may be prepared by O-alkylation of oxime derivatives of formula VIb with a compound of formula VII, in which $R_4$ is $C_1$-$C_4$alkyl or $C_1$-$C_4$halogenalkyl and X represents a leaving group, such as halogen, mesylate or tosylate, in the presence of a base. The alkylation reaction is advantageously carried out in aprotic inert organic solvents. Such solvents are hydrocarbons such as benzene, toluene, xylene or cyclohexane, ethers such as diethyl ether, ethylene glycol dimethyl ether, diethylene glycol dimethyl ether, tetrahydrofuran or dioxane, amides such as N,N-dimethylformamide, diethylformamide or N-methylpyrrolidinone. The reaction temperatures are between −20° C. and +120° C. Suitable bases are inorganic bases such as hydrides, e.g. sodium hydride or calcium hydride, hydroxides, e.g. sodium hydroxide or potassium hydroxide, carbonates such as sodium carbonate and potassium carbonate, or hydrogen carbonates such as potassium hydrogen carbonate and sodium hydrogen carbonate may also be used as bases. The bases can be used as such or else with catalytic amounts of a phase-transfer catalyst, for example crown ether, in particular 18-crown-6, or a tetraalkylammonium salt. O-Alkylhydroxylamines of formula IIA may be prepared by the reduction of O-alkoxy oxime derivatives of formula VI. It will be appreciated by those skilled in the art that this reduction can be carried out with a number of different reducing agents.

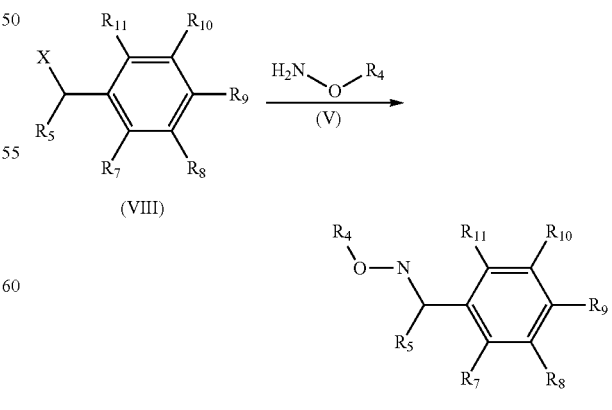

O-Alkylhydroxylamines of formula IIA may also prepared by the nucleophilic substitution of benzylic derivatives of formula VIII, in which $R_5$, $R_7$, $R_8$, $R_9$, $R_{10}$ and $R_{11}$ are as defined under formula I and X represents a leaving group, such as halogen, mesylate or tosylate, with a compound of formula V, in which $R_4$ is $C_1$-$C_4$alkyl or $C_1$-$C_4$halogenalkyl, in the presence of a base. The substitution reaction is advantageously carried out in aprotic inert organic solvents. The reaction temperatures are between 0° C. and +100° C. Suitable bases are, in particular pyridine, tertiary amines such as trimethylamine, triethylamine, huenig base, quinuclidine, 1,4-diazabicyclo[2.2.2]octane, 1,5-diazabicyclo[4.3.0]non-5-ene or 1,5-diazabicyclo[5.4.0]undec-7-ene. However, inorganic bases such as carbonates, sodium carbonate and potassium carbonate, or hydrogen carbonates such as potassium hydrogen carbonate and sodium hydrogen carbonate may also be used as bases. The bases can be used as such or else with catalytic amounts of a phase-transfer catalyst, for example crown ether, in particular 18-crown-6, or a tetraalkylammonium salt.

The compounds I and, where appropriate, the tautomers thereof, can, if appropriate, also be obtained in the form of hydrates and/or include other solvents, for example those which may have been used for the crystallization of compounds which are present in solid form.

It has now been found that the compounds of formula I according to the invention have, for practical purposes, a very advantageous spectrum of activities for protecting useful plants against diseases that are caused by phytopathogenic microorganisams, such as fungi, bacteria or viruses.

The invention relates to a method of controlling or preventing infestation of useful plants by phytopathogenic microorganisms, wherein a compound of formula I is applied as active ingredient to the plants, to parts thereof or the locus thereof. The compounds of formula I according to the invention are distinguished by excellent activity at low rates of application, by being well tolerated by plants and by being environmentally safe. They have very useful curative, preventive and systemic properties and are used for protecting numerous useful plants. The compounds of formula I can be used to inhibit or destroy the diseases that occur on plants or parts of plants (fruit, blossoms, leaves, stems, tubers, roots) of different crops of useful plants, while at the same time protecting also those parts of the plants that grow later e.g. from phytopathogenic microorganisms.

It is also possible to use compounds of formula I as dressing agents for the treatment of plant propagation material, in particular of seeds (fruit, tubers, grains) and plant cuttings (e.g. rice), for the protection against fungal infections as well as against phytopathogenic fungi occurring in the soil.

Furthermore the compounds of formula I according to the invention may be used for controlling fungi in related areas, for example in the protection of technical materials, including wood and wood related technical products, in food storage or in hygiene management.

The compounds of formula I are, for example, effective against the phytopathogenic fungi of the following classes: Fungi imperfecti (e.g. *Botrytis, Pyricularia, Helminthosporium, Fusarium, Septoria, Cercospora* and *Alternaria*) and Basidiomycetes (e.g. *Rhizoctonia, Hemileia, Puccinia*). Additionally, they are also effective against the Ascomycetes classes (e.g. *Venturia* and *Erysiphe, Podosphaera, Monilinia, Uncinula*) and of the *Oomycetes* classes (e.g. *Phytophthora, Pythium, Plasmopara*). Outstanding activity has been observed against powdery mildew (*Erysiphe* spp.). Furthermore, the novel compounds of formula I are effective against phytopathogenic bacteria and viruses (e.g. against *Xanthomonas* spp, *Pseudomonas* spp, *Erwinia amylovora* as well as against the tobacco mosaic virus). Good activity has been observed against Asian soybean rust (*Phakopsora pachyrhizi*).

Within the scope of the invention, useful plants to be protected typically comprise the following species of plants: cereal (wheat, barley, rye, oat, rice, maize, sorghum and related species); beet (sugar beet and fodder beet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (pumpkins, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, cinnamomum, camphor) or plants such as tobacco, nuts, coffee, eggplants, sugar cane, tea, pepper, vines, hops, bananas and natural rubber plants, as well as ornamentals.

The term "useful plants" is to be understood as including also useful plants that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors or PPO (protoporphyrinogen-oxidase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The term "useful plants" is to be understood as including also useful plants which have been so transformed by the use of recombinant DNA techniques that they are capable of synthesising one or more selectively acting toxins, such as are known, for example, from toxin-producing bacteria, especially those of the genus *Bacillus*.

Examples of such plants are: YieldGard® (maize variety that expresses a CrylA(b) toxin); YieldGard Rootworm® (maize variety that expresses a CryIIIB(b1) toxin); YieldGard Plus® (maize variety that expresses a CrylA(b) and a CryIIIB (b1) toxin); Starlink® (maize variety that expresses a Cry9(c) toxin); Herculex I® (maize variety that expresses a CryIF(a2) toxin and the enzyme phosphinothricine N-acetyltransferase (PAT) to achieve tolerance to the herbicide glufosinate ammonium); NuCOTN 33B® (cotton variety that expresses a Cry-1A(c) toxin); Bollgard I® (cotton variety that expresses a CrylA(c) toxin); Bollgard II® (cotton variety that expresses a CrylA(c) and a CryIIA(b) toxin); VIPCOT® (cotton variety that expresses a VIP toxin); NewLeaf® (potato variety that expresses a CrylIIA toxin); Nature-Gard® Agrisure® GT Advantage (GA21 glyphosate-tolerant trait), Agrisure® CB Advantage (Bt11 corn borer (CB) trait), Agrisure® RW (corn rootworm trait) and Protecta®.

The term "useful plants" is to be understood as including also useful plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818, and EP-A-0 353 191. The methods of producing such transgenic plants are generally known to the person skilled in the art and are described, for example, in the publications mentioned above.

The term "locus" of a useful plant as used herein is intended to embrace the place on which the useful plants are growing, where the plant propagation materials of the useful plants are sown or where the plant propagation materials of the useful plants will be placed into the soil. An example for such a locus is a field, on which crop plants are growing.

The term "plant propagation material" is understood to denote generative parts of the plant, such as seeds, which can be used for the multiplication of the latter, and vegetative material, such as cuttings or tubers, for example potatoes. There may be mentioned for example seeds (in the strict sense), roots, fruits, tubers, bulbs, rhizomes and parts of plants.

Germinated plants and young plants which are to be transplanted after germination or after emergence from the soil, may also be mentioned. These young plants may be protected before transplantation by a total or partial treatment by immersion. Preferably "plant propagation material" is understood to denote seeds.

The compounds of formula I can be used in unmodified form or, preferably, together with carriers and adjuvants conventionally employed in the art of formulation.

Therefore the invention also relates to compositions for controlling and protecting against phytopathogenic microorganisms, comprising a compound of formula I and an inert carrier, and to a method of controlling or preventing infestation of useful plants by phytopathogenic microorganisms, wherein a composition, comprising a compound of formula I as acitve ingredient and an inert carrier, is applied to the plants, to parts thereof or the locus thereof.

To this end compounds of formula I and inert carriers are conveniently formulated in known manner to emulsifiable concentrates, coatable pastes, directly sprayable or dilutable solutions, dilute emulsions, wettable powders, soluble powders, dusts, granulates, and also encapsulations e.g. in polymeric substances. As with the type of the compositions, the methods of application, such as spraying, atomising, dusting, scattering, coating or pouring, are chosen in accordance with the intended objectives and the prevailing circumstances. The compositions may also contain further adjuvants such as stabilizers, antifoams, viscosity regulators, binders or tackifiers as well as fertilizers, micronutrient donors or other formulations for obtaining special effects.

Suitable carriers and adjuvants can be solid or liquid and are substances useful in formulation technology, e.g. natural or regenerated mineral substances, solvents, dispersants, wetting agents, tackifiers, thickeners, binders or fertilizers. Such carriers are for example described in WO 97/33890.

The compounds of formula I or compositions, comprising a compound of formula I as active ingredient and an inert carrier, can be applied to the locus of the plant or plant to be treated, simultaneously or in succession with further compounds. These further compounds can be e.g. fertilizers or micronutrient donors or other preparations which influence the growth of plants. They can also be selective herbicides as well as insecticides, fungicides, bactericides, nematicides, molluscicides or mixtures of several of these preparations, if desired together with further carriers, surfactants or application promoting adjuvants customarily employed in the art of formulation.

A preferred method of applying a compound of formula I, or a composition, comprising a compound of formula I as active ingredient and an inert carrier, is foliar application. The frequency of application and the rate of application will depend on the risk of infestation by the corresponding pathogen. However, the compounds of formula I can also penetrate the plant through the roots via the soil (systemic action) by drenching the locus of the plant with a liquid formulation, or by applying the compounds in solid form to the soil, e.g. in granular form (soil application). In crops of water rice such granulates can be applied to the flooded rice field. The compounds of formula I may also be applied to seeds (coating) by impregnating the seeds or tubers either with a liquid formulation of the fungicide or coating them with a solid formulation.

A formulation, i.e. a composition comprising the compound of formula I and, if desired, a solid or liquid adjuvant, is prepared in a known manner, typically by intimately mixing and/or grinding the compound with extenders, for example solvents, solid carriers and, optionally, surface-active compounds (surfactants).

The agrochemical formulations will usually contain from 0.1 to 99% by weight, preferably from 0.1 to 95% by weight, of the compound of formula I, 99.9 to 1% by weight, preferably 99.8 to 5% by weight, of a solid or liquid adjuvant, and from 0 to 25% by weight, preferably from 0.1 to 25% by weight, of a surfactant.

Whereas it is preferred to formulate commercial products as concentrates, the end user will normally use dilute formulations.

Advantageous rates of application are normally from 5 g to 2 kg of active ingredient (a.i.) per hectare (ha), preferably from 10 g to 1 kg a.i./ha, most preferably from 20 g to 600 g a.i./ha. When used as seed drenching agent, convenient rates of application are from 10 mg to 1 g of active substance per kg of seeds. The rate of application for the desired action can be determined by experiments. It depends for example on the type of action, the developmental stage of the useful plant, and on the the application (location, timing, application method) and can, owing to these parameters, vary within wide limits.

Said methods may provide unexpectedly improved control of diseases compared to using the compounds of formula I in the absence of glyphosate. Said methods may be effective at enhancing the control of disease by compounds of formula I. While the mixture of glyphosate and at least one compound of formula I may increase the disease spectrum controlled, at least in part, by the compound of formula I, an increase in the activity of the compound of formula I on disease species already known to be controlled to some degree by the compound of formula I can also be the effect observed.

Said methods are particularly effective against the phytopathogenic organisms of the kingdom Fungi, phylum Basidiomycot, class Uredinomycetes, subclass Urediniomycetidae and the order Uredinales (commonly referred to as rusts). Species of rusts having a particularly large impact on agriculture include those of the family Phakopsoraceae, particularly those of the genus *Phakopsora*, for example *Phakopsora pachyrhizi*, which is also referred to as Asian soybean rust, and those of the family Pucciniaceae, particularly those of the genus *Puccinia* such as *Puccinia graminis*, also known as stem rust or black rust, which is a problem disease in cereal crops and *Puccinia recondita*, also known as brown rust.

An embodiment of said method is a method of protecting crops of useful plants against attack by a phytopathogenic organism and/or the treatment of crops of useful plants infested by a phytopathogenic organism, said method comprising simultaneously applying glyphosate, including salts or esters thereof, and at least one compound of formula I, which has activity against the phytopathogenic organism to at least one member selected from the group consisting of the plant, a part of the plant and the locus of the plant.

The compounds of formula (I), or a pharmaceutical salt thereof, described above may also have an advantageous spectrum of activity for the treatment and/or prevention of microbial infection in an animal. "Animal" can be any animal, for example, insect, mammal, reptile, fish, amphibian, preferably mammal, most preferably human. "Treatment" means the use on an animal which has microbial infection in order to reduce or slow or stop the increase or spread of the infection, or to reduce the infection or to cure the infection. "Prevention" means the use on an animal which has no apparent signs of microbial infection in order to prevent any future infection, or to reduce or slow the increase or spread of any future infection. According to the present invention there is provided the use of a compound of formula (I) in the manufacture of a medicament for use in the treatment and/or prevention of microbial infection in an animal. There is also provided the use of a compound of formula (I) as a pharmaceutical agent. There is also provided the use of a compound of formula (I) as an antimicrobial agent in the treatment of an animal. According to the present invention there is also provided a pharmaceutical composition comprising as an active ingredient a compound of formula (I), or a pharmaceutically acceptable salt thereof, and a pharmaceutically acceptable diluent or carrier. This composition can be used for the treatment and/or prevention of antimicrobial infection in an animal. This pharmaceutical composition can be in a form suitable for oral administration, such as tablet, lozenges, hard capsules, aqueous suspensions, oily suspensions, emulsions dispersible powders, dispersible granules, syrups and elixirs. Alternatively this pharmaceutical composition can be in a form suitable for topical application, such as a spray, a cream or lotion. Alternatively this pharmaceutical composition can be in a form suitable for parenteral administration, for example injection. Alternatively this pharmaceutical composition can be in inhalable form, such as an aerosol spray. The compounds of formula (I) may be effective against various microbial species able to cause a microbial infection in an animal. Examples of such microbial species are those causing Aspergillosis such as *Aspergillus fumigatus*, *A. flavus*, *A. terrus*, *A. nidulans* and *A. niger*; those causing Blastomycosis such as *Blastomyces dermatitidis*; those causing Candidiasis such as *Candida albicans*, *C. glabrata*, *C. tropicalis*, *C. parapsilosis*, *C. krusei* and *C. lusitaniae*; those causing Coccidioidomycosis such as *Coccidioides immitis*; those causing Cryptococcosis such as *Cryptococcus neoformans*; those causing Histoplasmosis such as *Histoplasma capsulatum* and those causing Zygomycosis such as *Absidia corymbifera*, *Rhizomucor pusillus* and *Rhizopus arrhizus*. Further examples are *Fusarium* Spp such as *Fusarium oxysporum* and *Fusarium solani* and *Scedosporium* Spp such as *Scedosporium apiospermum* and *Scedosporium prolificans*. Still further examples are *Microsporum* Spp, *Trichophyton* Spp, *Epidermophyton* Spp, *Mucor* Spp, *Sporothorix* Spp, *Phialophora* Spp, *Cladosporium* Spp, *Petriellidium* spp, *Paracoccidioides* Spp and *Histoplasma* Spp.

The following non-limiting Examples illustrate the above-described invention in greater detail without limiting it.

PREPARATION EXAMPLES

Example P1

Preparation of 3-difluoromethyl-1-methyl-1H-pyrazole-4-carboxylic acid (2,4-dichlorobenzyl)-methoxy-amide (compound 1.091)

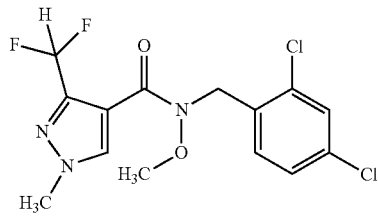 [SMILES: CON(Cc1ccc(Cl)cc1Cl)C(=O)c1cn(C)nc1C(F)F]

A solution of 3-difluoromethyl-1-methyl-1H-pyrazole-4-carbonyl chloride (292 mg; 1.5 mmol) in dichloromethane (3 ml) was added dropwise to a stirred solution of N-(2,4-dichloro-benzyl)-O-methyl-hydroxylamine (309 mg; 1.5 mmol), prepared as described in example P10b, triethylamine (0.41 ml; 3.0 mmol) in dichloromethane (8 ml) at 0° C. The reaction mixture was stirred for 3 hours at ambient temperature. The reaction mixture was washed with 1M NaOH (20 ml), 1M HCl (20 ml) brine (20 ml) and then dried over $Na_2SO_4$. After removal of the sol the residue was purified by flash chromatography over silica gel (eluant: α-hexane/ethyl acetate 6:4).

0.49 g (89.7% of theory) of 3-difluoromethyl-1-methyl-1H-pyrazole-4-carboxylic acid (2,4-dichlorobenzyl)-methoxy-amide was obtained in form of a resin.

$^1$H NMR: ($CDCl_3$, 400 MHz):
3.68 (s, 3H); 3.98 (s, 3H); 5.04 (s, 2H); 7.15-7.43 (m, 4H); 7.93 (s, 1H).
MS $[M+H]^+$ 364/366/368.

Example P2

3-Difluoromethyl-1-methyl-1H-pyrazole-4-carboxylic acid [1-(3-iodo-phenyl)-ethyl]-methoxy-amide (compound 1.014)

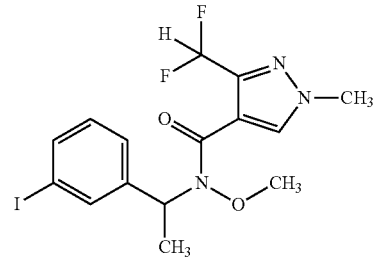 [SMILES: CON(C(=O)c1cn(C)nc1C(F)F)C(C)c1cccc(I)c1]

To a solution of N-[1-(3-iodo-phenyl)-ethyl]-O-methyl-hydroxylamine (3 g, 10.8 mmol), prepared as described in example P11, in dichloromethane (30 ml), was added triethylamine (2.5 ml, 26.3 mmol) followed by a solution of 3-difluoromethyl-1-methyl-1H-pyrazole-4-carbonyl chloride (2.2 g, 11.3 mmol) slowly at 0° C. After complete addition of acid chloride, the reaction mixture was stirred overnight at ambient temperature. The reaction mixture was diluted with water (100 ml) and extracted with dichloromethane (3×60 ml). The combined dichloromethane layer was washed with 2N HCl, sat. $NaHCO_3$ and brine, dried over anh. sodium sulfate and concentrated. The crude mass was purified by column chromatography using 35% ethyl acetate in hexane to yield 2.7 g (60% of theory) of 3-difluoromethyl-1-methyl-1H-pyrazole-4-carboxylic acid [1-(3-iodo-phenyl)-ethyl]methoxy-amide in form of a solid. Mp 136-138° C.

$^1$H NMR (400 MHz, CDCl3): 1.64-1.66 (d, 3H); 3.45 (s, 3H); 3.96 (s, 3H); 5.73-5.78 (m, 1H); 7.05-7.43 (t, 1H CHF2); 7.23 (s, 1H); 7.41-7.43 (d, 1H); 7.61-7.63 (s, 1H); 7.79 (s, 1H)
MS [M+H]$^+$:436.09/437.27.

Example P3

Preparation of 3-difluoromethyl-1-methyl-1H-pyrazole-4-carboxylic acid [1-(4' chloro-biphenyl-3-yl)-ethyl]-methoxy-amide (compound 1.019)

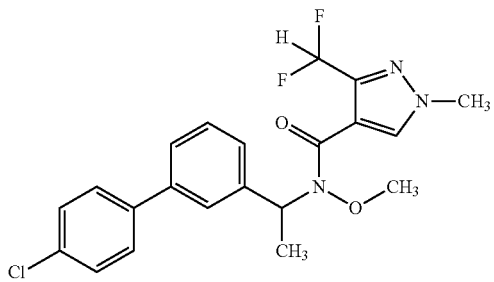 [SMILES: CON(C(=O)c1cn(C)nc1C(F)F)C(C)c1cccc(-c2ccc(Cl)cc2)c1]

To a stirred solution of 3-difluoromethyl-1-methyl-1H-pyrazole-4-carboxylic acid [1-(3-iodo-phenyl)-ethyl]-methoxy-amide (0.2 g, 0.46 mmol), prepared as described in example P2, in a mixture of ethanol (12 ml) and water (4 ml) was added, 4-chloro-phenyl boronic acid (0.079 g, 0.5 mmol) followed by palladium acetate (0.052 g, 0.23 mmol) and potassium carbonate (0.19 g, 1.38 mmol). It was stirred for 18 hours at ambient temperature. Reaction mass was filtered on celite bed then diluted with water and extracted in ethyl acetate (3×60 ml), washed with water, brine and dried over anhydrous sodium sulfate. The crude mass was purified by column chromatography using 36% Ethyl acetate in hexane to yield 0.09 g (50% of theory) of 3-Difluoromethyl-1-methyl-1H-pyrazole-4-carboxylic acid [1-(4' chloro-biphenyl-3-yl)-ethyl]-methoxy-amide in form of a resin.

$^1$H NMR (CDCl3, 400 MHz): 1.68-1.70 (d, 3H); 3.57 (s, 3H); 3.92 (s, 3H); 5.69-5.75 (m, 1H); 7.13-7.40 (t, 1H CHF2); 7.44-7.47 (d, 2H); 7.51-7.53 (d, 2H); 7.57-7.59 (d, 1H); 7.65-7.67 (d, 2H); 7.68 (s, 1H); 8.33 (s, 1H)
MS [M+H]$^+$:419.87/420.51/422.23

Example P4

Preparation of 3-difluoromethyl-1-methyl-1H-pyrazole-4-carboxylic acid [1-(3',4'-dichloro-biphenyl-3-yl)-ethyl]-methoxy-amide (compound 1.020)

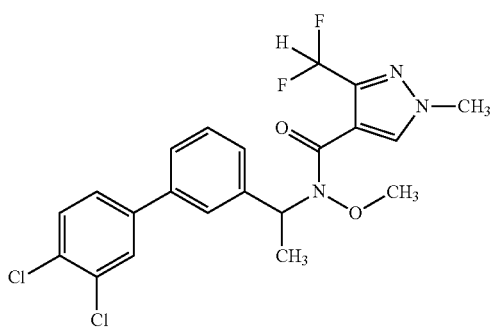 [SMILES: CON(C(=O)c1cn(C)nc1C(F)F)C(C)c1cccc(-c2ccc(Cl)c(Cl)c2)c1]

To a stirred solution of 3-difluoromethyl-1-methyl-1H-pyrazole-4-carboxylic acid [1-(3-iodo-phenyl)-ethyl]-methoxy-amide (0.2 g, 0.46 mmol), prepared as described in example P2, in a mixture of ethanol (12 ml) and water (4 ml) was added, 3,4-dichloro-phenyl boronic acid (0.096 g, 0.5 mmol) followed by palladium acetate (0.052 g, 0.23 mmol) and potassium carbonate (0.19 g, 1.38 mmol). It was stirred for 18 hours at ambient temperature. Reaction mass was filtered on celite bed then diluted with water and extracted in ethyl acetate (3×60 ml), washed with water, brine and dried over anhydrous sodium sulfate). The crude mass was purified by column chromatography using 36% Ethyl acetate in hexane to yield 0.12 g (60% of theory) of 3-Difluoromethyl-1-methyl-1H-pyrazole-4-carboxylic acid [1-(3',4'-dichloro-biphenyl-3-yl)-ethyl]-methoxy-amide in form of a solid. Mp 162-164° C.

$^1$H NMR (CDCl3, 400 MHz): 1.75-1.76 (d, 3H); 3.64 (s, 3H); 3.98 (s, 3H); 5.76-5.81 (m, 1H); 7.19-7.47 (t, 1H CHF2); 7.51-7.53 (d, 2H); 7.68-7.77 (m, 4H); 7.97 (s, 1H); 8.4 (s, 1H)
MS [M+H]$^+$453.93/455.76/457.7.

Example P5

Preparation of 3-difluoromethyl-1-methyl-1H-pyrazole-4-carboxylic acid {1-[3-(4-chloro-phenoxy)-phenyl]-ethyl}-methoxy-amide (compound 1.021)

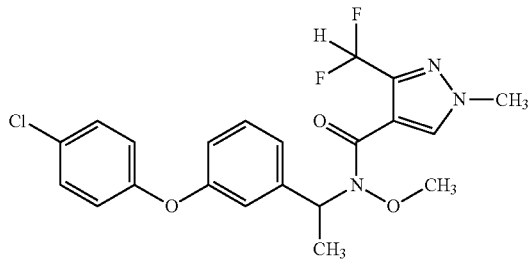

A mixture of 4-chlorophenol (0.2 g, 0.86 mmol) in DMF (2 ml), cesium carbonate (0.7 g, 1.14 mmol), N,N-dimethylglycine (0.01 g, 0.057 mmol), 3-difluoromethyl-1-methyl-1H-pyrazole-4-carboxylic acid [1-(3-iodo-phenyl)-ethyl]methoxy-amide (0.25 g, 0.57 mmol), and CuI (0.09 g, 0.024 mmol) was subjected to microwave irradiation at 90° C. for 20 minutes. Reaction mass was diluted with water and extracted with ethyl acetate (3×60 ml), washed with water, brine and dried over anhydrous sodium sulfate. The crude mass was purified by chromatography to yield 0.057 g (28% of theory) of 3-difluoromethyl-1-methyl-1H-pyrazole-4-carboxylic acid {1-[3-(4-chloro-phenoxy)-phenyl]-ethyl}-methoxy-amide in form of a resin.

$^1$H NMR (CDCl3, 400 MHz): 1.60-1.62 (d, 3H); 3.55 (s, 3H); 3.92 (s, 3H); 5.60-5.66 (m, 1H); 6.92-6.95 (dd, 1H); 6.98-7.01 (dd, 2H); 7.05 (s, 1H); 7.11-7.36 (t, 1H CHF2); 7.18-7.2 (d, 1H); 7.38-7.40 (m, 3H); 8.29 (s, 1H)
MS [M+H]$^+$436.16/438.34

Example P6

Preparation of 3-difluoromethyl-1-methyl-1H-pyrazole-4-carboxylic acid [1-(4-iodo-phenyl)-ethyl]-methoxy-amide (compound 1.003)

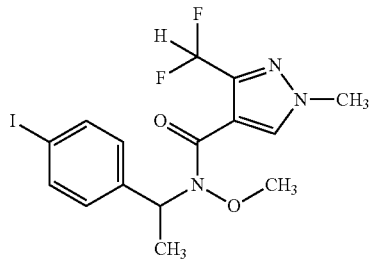 [SMILES: CON(C(=O)c1cn(C)nc1C(F)F)C(C)c1ccc(I)cc1]

To a stirred solution of N-[1-(4-Iodo-phenyl)-ethyl]-O-methyl-hydroxylamine (2.1 g, 7.57 mmol), prepared as described in example P12, in dichloromethane (25 ml) was added triethyl amine (3.15 ml, 22.68 mmol) followed by a solution of 3-Difluoromethyl-1-methyl-1H-pyrazole-4-carbonyl chloride (1.5 g, 7.94 mmol) in dichloromethane (5 ml) slowly in ice cold condition. The reaction mixture was stirred at ambient temperature for 16 h. Reaction mixture was poured into 40 ml ice-water. Aqueous layer was extracted with dichloromethane (2×40 ml). The combined organic layer was washed with 2(N) HCl(2×20 ml) followed by saturated sodium bicarbonate (2×20 ml) and dried over sodium sulfate. Organic layer was concentrated under vacuum to give light yellow liquid. Crude was purified by chromatography to afford 2.05 g (62% of theory) of 3-difluoromethyl-1-methyl-1H-pyrazole-4-carboxylic acid [1-(4-iodo-phenyl)ethyl]-methoxy-amide as white solid. Mp. 72-74° C.

$^1$H NMR (CDCl3, 400 MHz): 1.64-1.66 (d, 3H); 3.43 (s, 3H); 3.95 (s, 3H); 5.73-5.79 (m, 1H); 7.102-7.37 (t, 1H CHF2); 7.19-7.21 (d, 2H); 7.65-7.68 (dd, 2H); 7.83 (s, 1H)

MS [M+H]$^+$436.06/437.24

Example P7

Preparation of 3-difluoromethyl-1-methyl-1H-pyrazole-4-carboxylic acid {1-[4-(4-chloro-phenoxy)-phenyl]-ethyl}-methoxy-amide(compound 1.010)

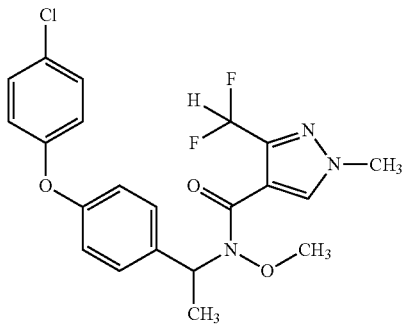 [SMILES: CON(C(=O)c1cn(C)nc1C(F)F)C(C)c1ccc(Oc2ccc(Cl)cc2)cc1]

A 5 ml microwave vial was charged with 3-difluoromethyl-1-methyl-1H-pyrazole-4-carboxylic acid [1-(4-iodo-phenyl)-ethyl]-methoxy-amide (0.5 g, 1.15 mmol), prepared as described in example P6, 4-chlorophenol (0.221 g, 1.724 mmol), cesium carbonate (0.75 g, 3 mmol), N,N-dimethyl glycine (0.019 g, 0.115 mmol) and DMF (5 ml) as solvent. The mixture was degassed by purging nitrogen for 5 minutes. After, copper iodide (0.011 g, 0.0574 mmol) was added. The microwave vial was then subjected to microwave irradiation (Biotage) at 100° C. for 50 min. Reaction mixture was cooled and diluted with water. The aqueous layer was extracted with EtOAC (3×60 ml). The combined organic layer was washed with saturated sodium chloride (3×40 ml) and dried over sodium sulfate. Organic layer was concentrated under vacuum to give the crude mass. The crude was purified by chromatography to afford 0.45 g (48% of theory) of 3-difluoromethyl-1-methyl-1H-pyrazole-4-carboxylic acid {1-[4-(4-chloro-phenoxy)-phenyl]-ethyl}-methoxy-amide in form of resin.

$^1$H NMR (CDCl3, 400 MHz): 1.66-1.68 (d, 3H); 3.44 (s, 3H); 3.96 (s, 3H); 5.78-5.84 (m, 1H); 6.91-6.99 (m, 4H); 7.11-7.41 (t, 1H CHF2); 7.24-7.26 (dd, 2H); 7.42-7.44 (d, 2H); 7.85 (s, 1H)

MS [M+H]$^+$436.07/438.27

Example P8

Preparation of 3-difluoromethyl-1,1-dimethyl-1H-pyrazole-4-carboxylic acid (3-iodo-benzyl)-methoxy-amide (compound 1.097)

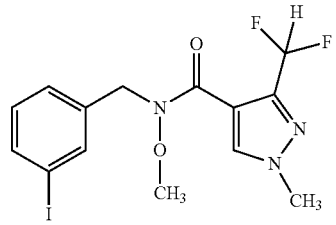 [SMILES: CON(Cc1cccc(I)c1)C(=O)c1cn(C)nc1C(F)F]

To a stirred solution of N-(3-Iodo-benzyl)-O-methyl-hydroxylamine (1 g, 3.6 mmol), prepared as described in example P13, in dichloromethane (10 ml) was added triethyl amine (1.25 ml, 9 mmol) followed by a solution of 3-difluoromethyl-1-methyl-1H-pyrazole-4-carbonyl chloride (0.74 g, 3.8 mmol) in dichloromethane (5 ml) slowly in ice cold condition. The reaction mixture was stirred at ambient temperature for 16 h. Reaction mixture was poured into 40 ml ice-water. Aqueous layer was extracted with dichloromethane (2×40 ml). The combined organic layer was washed with 2N HCl (2×20 ml) followed by saturated sodium bicarbonate (2×20 ml) and dried over sodium sulfate. Organic layer was concentrated under vacuum to give light yellow liquid. Crude was purified by chromatography to afford 1.3 g (87% of theory) of 3-difluoromethyl-1,1-dimethyl-1H-pyrazole-4-carboxylic acid (3-iodo-benzyl)-methoxy-amide in form of a solid. Mp 114-116° C.

$^1$H NMR (CDCl3, 400 MHz): 3.7 (s, 3H); 3.93 (s, 3H); 4.88 (s, 2H); 7.13-7.45 (t, 1H CHF2); 7.15-7.18 (m, 2H); 7.64-7.68 (dd, 2H); 8.36 (s, 1H)

MS [M+H]$^+$422.03/423.21

Example P9

Preparation of 3-difluoromethyl-1-methyl-1H-pyrazole-4-carboxylic acid (4'-chloro-biphenyl-3-ylmethyl)-methoxy-amide(compound 1.098)

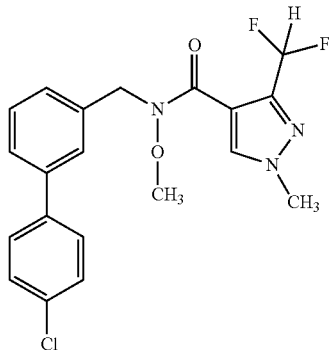 [SMILES: CON(Cc1cccc(-c2ccc(Cl)cc2)c1)C(=O)c1cn(C)nc1C(F)F]

To a stirred solution of 3-difluoromethyl-1,1-dimethyl-1H-pyrazole-4-carboxylic acid (3-iodo-benzyl)-methoxy-amide (0.1 g, 0.24 mmol), prepared as described in example P8, in a mixture of ethanol: water (10 ml, 3:1) was added 4-chloro boronic acid (0.04 g, 0.26 mmol) followed by palladium acetate (0.027 g, 0.12 mmol) and potassium carbonate (0.099 g, 0.72 mmol). The reaction mixture was stirred 12 hours at ambient temperature. Reaction mass was filtered on celite bed, diluted with water. Aqueous layer was extracted with EtOAc (3×30 ml). The combined organic layer was washed with brine (2×30 ml) and dried over sodium sulfate. Organic layer was concentrated under vacuum to give crude mass, which was purified by chromatography to afford 0.28 g (35% of theory) of 3-difluoromethyl-1-methyl-1H-pyrazole-4-carboxylic acid (4'-chloro-biphenyl-3-ylmethyl)-methoxy-amide in form of a solid. Mp 78-80° C.

$^1$H NMR (CDCl3, 400 MHz): 3.72 (s, 3H); 3.93 (s, 3H); 4.98 (s, 2H); 7.196-7.42 (t, 1H CHF2); 7.31 (s, 1H); 7.44-7.46 (d, 1H); 7.51-7.53 (dd, 2H); 7.57-7.6 (m, 2H); 7.64-7.66 (dd, 2H); 8.35 (s, 1H)

MS [M+H]$^+$420.17

Example P10

Preparation of N-(2,4-dichloro-benzyl)-O-methyl-hydroxylamine a) Preparation of 2,4-dichloro-benzaldehyde O-methyl-oxime

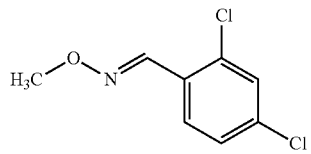

A solution of 2,4-dichloro-benzaldehyde (10.0 g, 57.1 mmole) in methanol (100 ml) was treated with pyridine (5.9 ml, 70 mmol) followed by O-methyl hydroxylamine hydrochloride (5.80 g, 70 mmol). The resulting mixture was stirred at 22° C. over night for 16 hours. The reaction mixture was poured onto water (200 ml) and extracted with dichloromethane (3×50 ml). The organic layers were washed with brine and dried over anhydrous Na$_2$SO$_4$. After removal of the solvent the residue (12.17 g) was purified by flash chromatography over silica gel (eluent: α-hexane).

4.62 g (40% of theory) of 2,4-dichloro-benzaldehyde O-methyl-oxime was obtained in form of a white solid (m.p. 69-74° C.).

$^1$H NMR: (CDCl$_3$, 400 MHz):

3.97 (s, 3H); 7.23-7.26 (dd, 1H); 7.39-7.40 (d, 1H); 7.81-7.84 (d, 1H); 8.41 (s, 1H).

MS [M+H]$^+$204/206/208.

b) Preparation of N-(2,4-dichloro-benzyl)-O-methyl-hydroxylamine

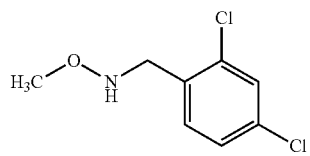

A solution of 2,4-dichloro-benzaldehyde O-methyl-oxime (1.0 g, 4.9 mmol), prepared as described in example P10a, in acetic acid (7.1 ml) was treated at 10° C. with sodium cyanoborohydride (615 mg, 9.8 mmol) added in small portions over 10 minutes and the resulting solution was stirred at 24° C. for 7 hours. The solvent was evaporated under reduced pressure (co-evaporation with toluene twice) and the residue was slurried with water. The aqueous phase was extracted with dichloromethane (2×20 ml), washed with brine and dried over anhydrous Na$_2$SO$_4$. After removal of the solvent, the residue (1510 mg) was purified by flash chromatography over silica gel (eluent: c-hexane/ethyl acetate 9:1). 690 mg (68.0% of theory) of N-(2,4-dichloro-benzyl)-O-methyl-hydroxylamine was obtained in form of a clear liquid.

$^1$H NMR: (CDCl$_3$, 400 MHz):

3.52 (s, 3H); 4.13 (s$_{br}$, 2H); 5.86 (s$_{br}$, 1H); 7.22-7.26 (dd, 1H); 7.35-7.38 (d, 1H); 7.39-7.39 (dd, 1H).

MS [M+H]$^+$ 206/208/210.

b2) Preparation of N-(2,4-dichloro-benzyl)-O-methyl-hydroxylamine

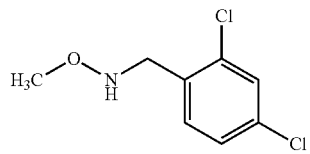

A solution of O-methyl hydroxylamine hydrochloride (2.51 g, 30 mmol) in DMF (10 ml) was treated at 10° C. with Huenigs base (1.75 ml, 10.0 mmol) followed by addition of 2,4-dichloro-1-chloromethyl-benzene (1.99 g, 10 mmol). The resulting mixture was stirred at 24° C. for 6 hours, diluted with ethylacetate (50 ml), washed with brine and dried over anhydrous Na$_2$SO$_4$. The solvent was evaporated under reduced pressure (40 mbar; 45° C.).

860 mg (41.7% of theory) of N-(2,4-dichloro-benzyl)-O-methyl-hydroxylamine was obtained as a mixture with 2,4-dichloro-1-chloromethyl-benzene in form of a liquid.

Example P11

Preparation of
N-[1-(3-iodo-phenyl)-ethyl]-O-methyl-hydroxylamine

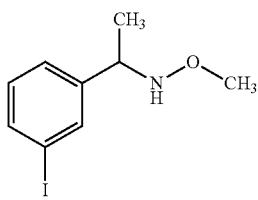

To a solution of O-methyl hydroxylamine hydrochloride (2.5 g, 30.48 mmol) in methanol (25 ml), was added triethylamine (30.48 mmoles) followed by 3-iodo acetophenone (5 g, 20.3 mmol) and the mixture was heated at 60° C. for 3 hours. On completion of the reaction, the mixture was concentrated to remove methanol, to give 1-(3-iodo-phenyl)-ethanone O-methyl-oxime (crude), which was dissolved in glacial acetic acid (50 ml). Sodium cyanoborohydride (2.5 g, 40 mmol) was added portion wise. The mixture was allowed to stir overnight at ambient temperature. The reaction mixture was concentrated to remove acetic acid and diluted with water. The aqueous layer was extracted with ethyl acetate (3×80 ml), the combined organic layer is washed with brine (40 ml) and dried over sodium sulphate. Organic layer was concentrated under vacuum to obtain 5.6 g crude material, which was subjected to column purification (60-120µ mesh silica gel, 15% ethyl acetate in hexane) to give 3.4 g (54% of theory) of N-[1-(3-Iodo-phenyl)-ethyl]-O-methyl-hydroxylamine.

$^1$H NMR (400 MHz, CDCl3): 1.23-1.24 (d, 3H); 3.379 (s, 3H); 3.99-4.04 (m, 1H); 5.51 (s, 1H); 7.02-7.06 (d, 2H); 7.57-7.60 (d, 2H)
MS [M+H]$^+$:278.12

Example P12

Preparation of
N-[1-(4-iodo-phenyl)-ethyl]-O-methyl-hydroxylamine

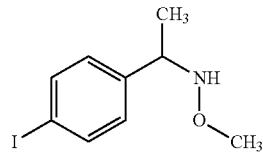

To a stirred solution of 4-iodo acetophenone (2.0 g, 8.13 mmol) in methanol (25 ml), O-methyl hydroxyl amine hydrochloride (0.7 g, 8.94 mmole) was added followed by triethyl amine (0.904 g, 8.94 mmol). The reaction mixture was stirred at ambient temperature for 4 hours. Reaction mixture was concentrated under vacuum, residual mass was diluted with water (50 ml) and aq. layer was extracted with ethyl acetate (3×30 ml). Organic layer was washed with water (2×30 ml) followed by brine solution, dried over anhydrous sodium sulfate and evaporated to obtain 2.17 g (97% of theory) of 1-(4-iodo-phenyl)-ethanone O-methyl-oxime.

To a stirred solution of 1-(4-iodo-phenyl)-ethanone O-methyl-oxime (2.17 g, 7.83 mmol) in glacial acetic acid (22 ml), Sodium cyano borohydride (1.54 g, 24.39 mmole) was added portion wise at 15° C. and stirred for 12 hours at ambient temperature. Acetic acid was removed by distillation. The resulting reaction mass was basified with 10% aq. NaOH solution at 10-15° C. Aqueous layer was extracted with EtOAc (3×30 ml). The combined organic layer was washed with brine (2×30 ml) and dried over sodium sulfate. The organic layer was concentrated under vacuum to give pale yellow liquid, which was purified by chromatography to afford 2.1 g (96% of theory) of N-[1-(4-Iodo-phenyl)-ethyl]-O-methyl-hydroxylamine.

$^1$H NMR (CDCl3, 400 MHz): 1.23-1.24 (d, 3H); 3.37 (s, 3H); 3.99-4.04 (m, 1H); 5.51 (s, 1H); 7.02-7.06 (d, 2H); 7.57-7.60 (d, 2H)

Example P13

Preparation of
N-(3-iodo-benzyl)-O-methyl-hydroxylamine

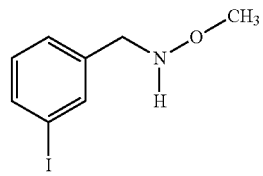

To a stirred solution of 3-iodo benzaldehyde (1 g, 4.3 mmol) in methanol (25 ml), O-methyl hydroxyl amine hydrochloride (0.54 g, 6.5 mmol) was added followed by triethyl amine (0.9 ml, 6.5 mmol). The reaction mixture was stirred at ambient temperature for 4 hours. Reaction mixture was concentrated under vacuum; residual mass was diluted with water (50 ml) and extracted with ethyl acetate (3×30 ml). Ethyl acetate layer was washed with water (2×30 ml) followed by brine solution, dried over anhydrous sodium sulfate and evaporated to obtain 3-Iodo-benzaldehyde O-methyl-oxime (crude), which was dissolved in glacial acetic acid (10 ml), followed by addition of sodium cyanoborohydride (0.54 g, 8.6 mmol) portion wise at 15° C. The mixture was stirred for 12 hrs at room temperature. Excess acetic acid was removed by distillation. Resulting reaction mass was basified with 10% aq. NaOH solution at 10-15° C. Aqueous layer was extracted with EtOAc (3×30 ml). The combined organic layer was washed with brine (2×30 ml) and dried over sodium sulfate. Organic layer was concentrated under vacuum to give crude mass, which was purified by chromatography to afford 1 g (89% of theory) of N-(3-Iodo-benzyl)-O-methyl-hydroxylamine $^1$H NMR (CDCl3, 400 MHz): 3.22-3.34 (d, 3H); 3.85-3.87 (d, 3H); 6.94-6.97 (t, 1H); 7.09-7.13 (t, 1H); 7.34-7.36 (d, 1H); 7.59-7.61 (d, 1H); 7.72 (s, 1H)
MS [M+H]$^+$264.1/265.14

Tables 1 to 3: Compounds of formula Ia:

The invention was further illustrated by the preferred individual compounds of formula (Ia) listed below in Tables 1 to 3. Characterising data is given in Table 5.

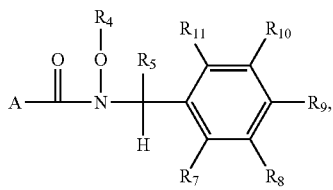
(Ia)

In the compounds of formula Ia, A is selected from the groups consisting of $A_1$,

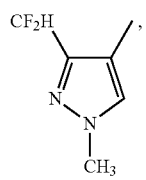
($A_1$)

$A_2$,

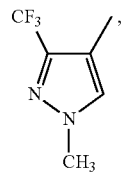
($A_2$)

and $A_3$,

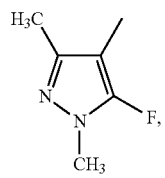
($A_3$)

and n is 0 or 1.

Each of Tables 1 to 3, which follow the Table Y below, comprises 100 compounds of formula (Ia) in which $R_4$, $R_5$, $R_7$, $R_8$, $R_9$, $R_{10}$ and $R_{11}$ have the values given in Table Y and A has the value given in the relevant Table 1 to 3. Thus Table 1 corresponds to Table Y when Y is 1 and A has the value given under the Table 1 heading, Table 2 corresponds to Table Y when Y is 2 and A has the value given under the Table 2 heading, and so on for Tables 3.

TABLE Y

| Cpd No. | $R_4$ | $R_5$ | $R_7$ | $R_8$ | $R_9$ | $R_{10}$ | $R_{11}$ |
|---|---|---|---|---|---|---|---|
| Y.001 | Me | Me | H | H | Cl | H | H |
| Y.002 | Me | Me | H | H | Br | H | H |
| Y.003 | Me | Me | H | H | I | H | H |
| Y.004 | Me | Me | H | H | $CH_3$ | H | H |
| Y.005 | Me | Me | H | H | $CF_3$ | H | H |
| Y.006 | Me | Me | H | H | C≡CH | H | H |
| Y.007 | Me | Me | H | H | t-Bu | H | H |
| Y.008 | Me | Me | H | H | 4-Cl-phenyl | H | H |
| Y.009 | Me | Me | H | H | 3,4-$Cl_2$-phenyl | H | H |
| Y.010 | Me | Me | H | H | 4-Cl-phenoxy | H | H |
| Y.011 | Me | Me | H | H | 3,4-$Cl_2$-phenoxy | H | H |
| Y.012 | Me | Me | H | Cl | H | H | H |
| Y.013 | Me | Me | H | Br | H | H | H |
| Y.014 | Me | Me | H | I | H | H | H |
| Y.015 | Me | Me | H | $CH_3$ | H | H | H |
| Y.016 | Me | Me | H | $CF_3$ | H | H | H |
| Y.017 | Me | Me | H | C≡CH | H | H | H |
| Y.018 | Me | Me | H | t-Bu | H | H | H |
| Y.019 | Me | Me | H | 4-Cl-phenyl | H | H | H |
| Y.020 | Me | Me | H | 3,4-$Cl_2$-phenyl | H | H | H |
| Y.021 | Me | Me | H | 4-Cl-phenoxy | H | H | H |
| Y.022 | Me | Me | H | 3,4-$Cl_2$-phenoxy | H | H | H |
| Y.023 | Me | Me | Cl | H | Cl | H | H |
| Y.024 | Me | Me | Cl | H | Br | H | H |
| Y.025 | Me | Me | Cl | H | I | H | H |
| Y.026 | Me | Me | Cl | H | $CH_3$ | H | H |
| Y.027 | Me | Me | Cl | H | $CF_3$ | H | H |
| Y.028 | Me | Me | Cl | H | C≡CH | H | H |
| Y.029 | Me | Me | Cl | H | t-Bu | H | H |
| Y.030 | Me | Me | Cl | H | 4-Cl-phenyl | H | H |
| Y.031 | Me | Me | Cl | H | 3,4-$Cl_2$-phenyl | H | H |
| Y.032 | Me | Me | Cl | H | 4-Cl-phenoxy | H | H |
| Y.033 | Me | Me | Cl | H | 3,4-$Cl_2$-phenoxy | H | H |
| Y.034 | Me | Me | Cl | Cl | H | H | H |
| Y.035 | Me | Me | Cl | Br | H | H | H |
| Y.036 | Me | Me | Cl | I | H | H | H |

TABLE Y-continued

| Cpd No. | R$_4$ | R$_5$ | R$_7$ | R$_8$ | R$_9$ | R$_{10}$ | R$_{11}$ |
|---|---|---|---|---|---|---|---|
| Y.037 | Me | Me | Cl | CH$_3$ | H | H | H |
| Y.038 | Me | Me | Cl | CF$_3$ | H | H | H |
| Y.039 | Me | Me | Cl | C≡CH | H | H | H |
| Y.040 | Me | Me | Cl | t-Bu | H | H | H |
| Y.041 | Me | Me | Cl | 4-Cl-phenyl | H | H | H |
| Y.042 | Me | Me | Cl | 3,4-Cl$_2$-phenyl | H | H | H |
| Y.043 | Me | Me | Cl | 4-Cl-phenoxy | H | H | H |
| Y.044 | Me | Me | Cl | 3,4-Cl$_2$-phenoxy | H | H | H |
| Y.045 | Me | Me | Cl | H | Cl | H | Cl |
| Y.046 | Me | Me | Cl | H | Br | H | Cl |
| Y.047 | Me | Me | Cl | H | I | H | Cl |
| Y.048 | Me | Me | Cl | H | CF$_3$ | H | Cl |
| Y.049 | Me | Me | Cl | H | C≡CH | H | Cl |
| Y.050 | Me | Me | Cl | H | t-Bu | H | Cl |
| Y.051 | Me | Me | Cl | H | 4-Cl-phenyl | H | Cl |
| Y.052 | Me | Me | Cl | H | 3,4-Cl$_2$-phenyl | H | Cl |
| Y.053 | Me | Me | Cl | H | 4-Cl-phenoxy | H | Cl |
| Y.054 | Me | Me | Cl | H | 3,4-Cl$_2$-phenoxy | H | Cl |
| Y.055 | Me | Me | Cl | Cl | H | H | Cl |
| Y.056 | Me | Me | Cl | Br | H | H | Cl |
| Y.057 | Me | Me | Cl | I | H | H | Cl |
| Y.058 | Me | Me | Cl | CF$_3$ | H | H | Cl |
| Y.059 | Me | Me | Cl | C≡CH | H | H | Cl |
| Y.060 | Me | Me | Cl | t-Bu | H | H | Cl |
| Y.061 | Me | Me | Cl | 4-Cl-phenyl | H | H | Cl |
| Y.062 | Me | Me | Cl | 3,4-Cl$_2$-phenyl | H | H | Cl |
| Y.063 | Me | Me | Cl | 4-Cl-phenoxy | H | H | Cl |
| Y.064 | Me | Me | Cl | 3,4-Cl$_2$-phenoxy | H | H | Cl |
| Y.065 | Me | Et | H | H | Cl | H | H |
| Y.066 | Me | Et | H | H | I | H | H |
| Y.067 | Me | Et | H | H | t-Bu | H | H |
| Y.068 | Me | Et | H | H | 4-Cl-phenyl | H | H |
| Y.069 | Me | Et | H | H | 4-Cl-phenoxy | H | H |
| Y.070 | Me | Et | Cl | H | Cl | H | H |
| Y.071 | Me | Et | Cl | H | Cl | H | Cl |
| Y.072 | Me | Et | Cl | H | I | H | H |
| Y.073 | Me | Et | Cl | H | I | H | Cl |
| Y.074 | Me | Et | Cl | H | 4-Cl-phenyl | H | H |
| Y.075 | Me | Et | Cl | H | 4-Cl-phenyl | H | Cl |
| Y.076 | Me | Et | Cl | H | 4-Cl-phenoxy | H | H |
| Y.077 | Me | Et | Cl | H | 4-Cl-phenoxy | H | Cl |
| Y.078 | Me | Et | H | Cl | H | H | H |
| Y.079 | Me | Et | H | I | H | H | H |
| Y.080 | Me | Et | H | t-Bu | H | H | H |
| Y.081 | Me | Et | H | 4-Cl-phenyl | H | H | H |
| Y.082 | Me | Et | H | 4-Cl-phenoxy | H | H | H |
| Y.083 | Me | Et | Cl | Cl | H | H | H |
| Y.084 | Me | Et | Cl | Cl | H | H | Cl |
| Y.085 | Me | Et | Cl | I | H | H | H |
| Y.086 | Me | Et | Cl | I | H | H | Cl |
| Y.087 | Me | Et | Cl | 4-Cl-phenyl | H | H | H |
| Y.088 | Me | Et | Cl | 4-Cl-phenyl | H | H | Cl |
| Y.089 | Me | Et | Cl | 4-Cl-phenoxy | H | H | H |
| Y.090 | Me | Et | Cl | 4-Cl-phenoxy | H | H | Cl |
| Y.091 | Me | H | Cl | H | Cl | H | H |
| Y.092 | Me | H | Cl | H | Cl | H | Cl |
| Y.093 | Me | H | H | H | I | H | H |
| Y.094 | Me | H | H | H | 4-Cl-phenyl | H | H |
| Y.095 | Me | H | H | H | 3,4-Cl$_2$-phenyl | H | H |
| Y.096 | Me | H | H | H | 4-Cl-phenoxy | H | H |
| Y.097 | Me | H | H | I | H | H | H |
| Y.098 | Me | H | H | 4-Cl-phenyl | H | H | H |
| Y.099 | Me | H | H | 3,4-Cl$_2$-phenyl | H | H | H |
| Y.100 | Me | H | H | 4-Cl-phenoxy | H | H | H |
| Y.101 | Me | Me | OMe | H | H | H | H |
| Y.102 | Me | Me | OH | Me | H | Me | H |
| Y.103 | Me | H | —C=C—C=C— | | H | H | H |
| Y.104 | Me | Me | —C=C—C=C— | | H | H | H |
| Y.105 | Me | H | H | —C=C—C=C— | | H | H |
| Y.106 | Me | Me | H | —C=C—C=C— | | H | H |
| Y.107 | Me | CH$_2$F | H | H | Cl | H | H |
| Y.108 | Me | CH$_2$F | Cl | H | Cl | H | H |
| Y.109 | Me | CH$_2$F | Cl | H | Cl | H | Cl |

Table 1 provides 109 compounds of formula (Ia), wherein A is $A_1$

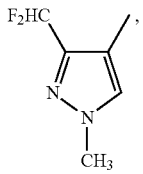
($A_1$)

and $R_4$, $R_5$, $R_7$, $R_8$, $R_9$, $R_{10}$ and $R_{11}$ are as defined in Table Y.

For example, compound 1.091 has the following structure:

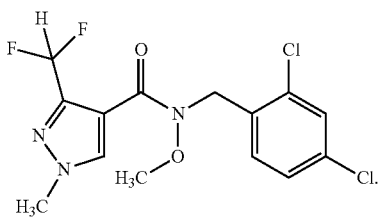
(1.091)

Table 2 provides 109 compounds of formula (Ia), wherein A is $A_2$

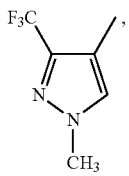
($A_2$)

and $R_4$, $R_5$, $R_7$, $R_8$, $R_9$, $R_{10}$ and $R_{11}$ are as defined in Table Y.

For example, compound 2.010 has the following structure:

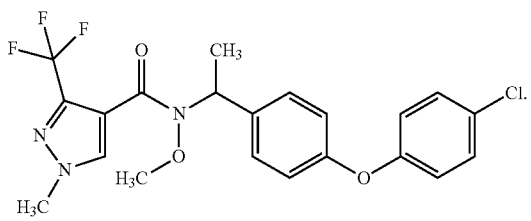
(2.010)

Table 3 provides 109 compounds of formula (Ia), wherein A is $A_3$

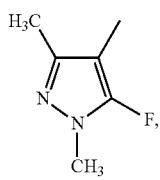
($A_3$)

and $R_4$, $R_5$, $R_7$, $R_8$, $R_9$, $R_{10}$ and $R_{11}$ are as defined in Table Y.

For example, compound 3.023 has the following structure:

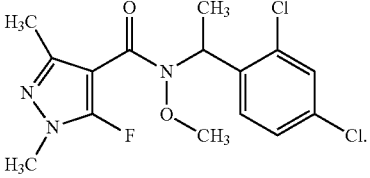
(3.023)

Table 4, which follow the Table Y above, comprises 109 compounds of formula (11b) in which $R_4$, $R_5$, $R_7$, $R_8$, $R_9$, $R_{10}$ and $R_{11}$ have the values given in Table Y.

Table 4 provides 109 compounds of formula (IIb)

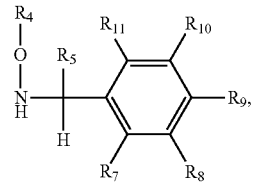
(IIb)

wherein $R_4$, $R_5$, $R_7$, $R_8$, $R_9$, $R_{10}$ and $R_{11}$ are as defined in Table Y.

Table 5: Characterising Data:

Table 5 shows selected melting point and selected NMR data for compounds of Table 1 to 3. $CDCl_3$ is used as the solvent for NMR measurements, unless otherwise stated. If a mixture of solvents is present, this is indicated as, for example: $CDCl_3/d_6$-DMSO). No attempt is made to list all characterising data in all cases.

In Table 5 and throughout the description that follows, temperatures are given in degrees Celsius; "NMR" means nuclear magnetic resonance spectrum; MS stands for mass spectrum; "%" is percent by weight, unless corresponding concentrations are indicated in other units. The following abbreviations are used throughout this description:

| | | | |
|---|---|---|---|
| m.p. = | melting point | b.p. = | boiling point. |
| S = | singlet | br = | broad |
| d = | doublet | dd = | doublet of doublets |
| t = | triplet | q = | quartet |
| m = | multiplet | ppm = | parts per million |

Compounds were analysed by LC-MS described below:
Method for LC-MS

| Method C | |
|---|---|
| MS | ZQ Mass Spectrometer from Waters (single quadrupole mass spectrometer), ionization method: electrospray, polarity: positive ionization, capillary (kV) 3.00, cone (V) 30.00, extractor (V) 3.00, source temperature (° C.) 100, desolvation temperature (° C.) 200, cone gas flow (L/Hr) 200, desolvation gas flow (L/Hr) 250, mass range: 150 to 800 Da. |
| LC | 1100er Series HPLC from Agilent: quaternary pump, heated column compartment and diode-array detector. Column: Waters Atlantis dc18; length: 20 mm; internal diameter: 3 mm; particle size: 3 µm, temperature (° C.) 40, DAD wavelength range (nm): 200 to 500, solvent gradient: A = 0.1% of formic acid in water and B: 0.1% of formic acid in acetonitrile. |

| Time (min) | A % | B % | Flow (ml/min) |
|---|---|---|---|
| 0.0 | 90 | 10 | 1.7 |
| 5.5 | 0.0 | 100 | 1.7 |
| 5.8 | 0.0 | 100 | 1.7 |
| 5.9 | 90 | 10 | 1.7 |

TABLE 5

| Cpd No. | 1H-NMR data: ppm (multiplicity/number of Hs) | MS [M + H]+ | m.p. (° C.) | LC-MS data T (min) [M + H]+ |
|---|---|---|---|---|
| 1.003 | 1.64-1.66 (d, 3H); 3.43 (s, 3H); 3.95 (s, 3H); 5.73-5.79 (m, 1H); 7.102-7.37 (t, 1H CHF2); 7.19-7.21 (d, 2H); 7.65-7.68 (dd, 2H); 7.83 (s, 1H) | 436.06/437.24 | 72-74 | |
| 1.007 | | | | 3.51 (366.18) |
| 1.010 | 1.66-1.68 (d, 3H); 3.44 (s, 3H); 3.96 (s, 3H); 5.78-5.84 (m, 1H); 6.91-6.99 (m, 4H); 7.11-7.41 (t, 1H CHF2); 7.24-7.26 (dd, 2H); 7.42-7.44 (d, 2H); 7.85 (s, 1H) | 436.07/438.27 | resin | |
| 1.014 | 1.64-1.66 (d, 3H); 3.45 (s, 3H); 3.96 (s, 3H); 5.73-5.78 (m, 1H); 7.05-7.43 (t, 1H CHF2); 7.23 (s, 1H); 7.41-7.43 (d, 1H); 7.61-7.63 (s, 1H); 7.79 (s, 1H); 7.29 (s, 1H) | 436.09/437.27 | 136-138 | |
| 1.016 | | | | 3.10 (378.06) |
| 1.019 | 1.68-1.70 (d, 3H); 3.57 (s, 3H); 3.92 (s, 3H); 5.69-5.75 (m, 1H); 7.13-7.40 (t, 1H CHF2); 7.44-7.47 (d, 2H); 7.51-7.53 (d, 2H); 7.57-7.59 (d, 1H); 7.65-7.67 (d, 2H); 7.68 (s, 1H); 8.33 (s, 1H) | 419.87/420.51/422.23 | resin | |
| 1.020 | 1.75-1.76 (d, 3H); 3.64 (s, 3H); 3.98 (s, 3H); 5.76-5.81 (m, 1H); 7.19-7.47 (t, 1H CHF2); 7.51-7.53 (d, 2H); 7.68-7.77 (m, 4H); 7.97 (s, 1H); 8.4 (s, 1H) | 453.93/455.76/457.7 | 162-164 | |
| 1.021 | 1.60-1.62 (d, 3H); 3.55 (s, 3H); 3.92 (s, 3H); 5.60-5.66 (m, 1H); 6.92-6.95 (dd, 1H); 6.98-7.01 (dd, 2H); 7.05 (s, 1H); 7.11-7.36 (t, 1H CHF2); 7.18-7.2 (d, 1H); 7.38-7.40 (m, 3H); 8.29 (s, 1H) | 436.16/438.34 | resin | |
| 1.023 | 1.65-1.69 (d, 3H); 3.41 (s, 3H); 3.97 (s, 3H); 6.00-6.05 (q, 1H); 7.10-7.40 (t, 1H CHF2); 7.24-7.29 (dd, 1H); 7.41-7.42 (d, 1H); 7.51-7.55 (d, 1H); 7.84 (s, 1H) | 378/380/382 | 135-141 | |
| 1.091 | 3.68 (s, 3H); 3.98 (s, 3H); 5.04 (s, 2H); 7.15-7.43 (m, 4H); 7.93 (s, 1H) | 364/366/368 | resin | |
| 1.092 | 3.58 (s, 3H); 3.94 (s, 3H); 5.27 (s, 2H); 7.11-7.42 (t, 1H); 7.37 (s, 2H); 7.86 (s, 1H) | 398/400/402 | 145-149 | |
| 1.096 | | | | 3.50 (422.02) |
| 1.097 | 3.7 (s, 3H); 3.93 (s, 3H); 4.88 (s, 2H); 7.13-7.45 (t, 1H CHF2); 7.15-7.18 (m, 2H); 7.64-7.68 (dd, 2H); 8.36 (s, 1H) | 422.03/423.21 | 114-116 | |
| 1.098 | 3.72 (s, 3H); 3.93 (s, 3H); 4.98 (s, 2H); 7.196-7.42 (t, 1H CHF2); 7.31 (s, 1H); 7.44-7.46 (d, 1H); 7.51-7.53 (dd, 2H); 7.57-7.6 (m, 2H); 7.64-7.66 (dd, 2H); 8.35 (s, 1H) | 420.17 | 78-80 | |
| 1.100 | | | | 3.45 (421.95) |
| 1.101 | | | | 2.47 (340.13) |
| 1.103 | | | | 2.76 (346.12) |
| 1.104 | | | | 3.16 (360.13) |
| 1.105 | | | | 2.79 (346.12) |
| 1.106 | | | | 3.13 (360.13) |
| 1.107 | 3.60 (s, 3 H), 3.97 (s, 3 H), 4.71-5.22 (m, 2 H), 5.76-5.87 (m, 1 H), 7.21 (t, J = 54.3 Hz, 1 H), 7.36 (d, J = 4.0 Hz, 4 H), 7.90 (s, 1 H) | 362/364 | 116-118 | |

Formulation examples for compounds of formula I:

Example F-1.1 to F-1.2

Emulsifiable Concentrates

| Components | F-1.1 | F-1.2 |
| --- | --- | --- |
| compound of Tables 1-6 | 25% | 50% |
| calcium dodecylbenzenesulfonate | 5% | 6% |
| castor oil polyethylene glycol ether (36 mol ethylenoxy units) | 5% | — |
| tributylphenolpolyethylene glycol ether (30 mol ethylenoxy units) | — | 4% |
| cyclohexanone | — | 20% |
| xylene mixture | 65% | 20% |

Emulsions of any desired concentration can be prepared by diluting such concentrates with water.

Example F-2

Emulsifiable Concentrate

| Components | F-2 |
| --- | --- |
| compound of Tables 1-6 | 10% |
| octylphenolpolyethylene glycol ether (4 to 5 mol ethylenoxy units) | 3% |
| calcium dodecylbenzenesulfonate | 3% |
| castor oil polyglycol ether (36 mol ethylenoxy units) | 4% |
| cyclohexanone | 30% |
| xylene mixture | 50% |

Emulsions of any desired concentration can be prepared by diluting such concentrates with water.

Examples F-3.1 to F-3.4

Solutions

| Components | F-3.1 | F-3.2 | F-3.3 | F-3.4 |
| --- | --- | --- | --- | --- |
| compound of Tables 1-6 | 80% | 10% | 5% | 95% |
| propylene glycol monomethyl ether | 20% | — | — | — |
| polyethylene glycol (relative molecular mass: 400 atomic mass units) | — | 70% | — | — |
| N-methylpyrrolid-2-one | — | 20% | — | — |
| epoxidised coconut oil | — | — | 1% | 5% |
| benzin (boiling range: 160-190°) | — | — | 94% | — |

The solutions are suitable for use in the form of microdrops.

Examples F-4.1 to F-4.4

Granulates

| Components | F-4.1 | F-4.2 | F-4.3 | F-4.4 |
| --- | --- | --- | --- | --- |
| compound of Tables 1-6 | 5% | 10% | 8% | 21% |
| kaolin | 94% | — | 79% | 54% |
| highly dispersed silicic acid | 1% | — | 13% | 7% |
| attapulgite | — | 90% | — | 18% |

The novel compound is dissolved in dichloromethane, the solution is sprayed onto the carrier and the solvent is then removed by distillation under vacuum.

Examples F-5.1 and F-5.2

Dusts

| Components | F-5.1 | F-5.2 |
| --- | --- | --- |
| compound of Tables 1-6 | 2% | 5% |
| highly dispersed silicic acid | 1% | 5% |
| talcum | 97% | — |
| kaolin | — | 90% |

Ready for use dusts are obtained by intimately mixing all components.

Examples F-6.1 to F-6.3

Wettable Powders

| Components | F-6.1 | F-6.2 | F-6.3 |
| --- | --- | --- | --- |
| compound of Tables 1-6 | 25% | 50% | 75% |
| sodium lignin sulfonate | 5% | 5% | — |
| sodium lauryl sulfate | 3% | — | 5% |
| sodium diisobutylnaphthalene sulfonate | — | 6% | 10% |
| octylphenolpolyethylene glycol ether (7 to 8 mol ethylenoxy units) | — | 2% | — |
| highly dispersed silicic acid | 5% | 10% | 10% |
| kaolin | 62% | 27% | — |

All components are mixed and the mixture is thoroughly ground in a suitable mill to give wettable powders which can be diluted with water to suspensions of any desired concentration.

Example F7

Flowable Concentrate for Seed Treatment

| | |
| --- | --- |
| compound of Tables 1-6 | 40% |
| propylene glycol | 5% |
| copolymer butanol PO/EO | 2% |
| tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Biological Examples

Fungicidal Action

Example B-1

Action against *Botrvtis cinerea*—fungal growth assay

Conidia of the fungus from cryogenic storage was directly mixed into nutrient broth (PDB potato dextrose broth). After placing a (DMSO) solution of the test compounds (0.002% active ingredient) into a microtiter plate (96-well format) the nutrient broth containing the fungal spores was added. The test plates were incubated at 24° C. and the inhibition of growth was measured photometrically after 3-4 days. The activity of a compound was expressed as fungal growth inhibition (0=no growth inhibition, ratings of 80% to 99% mean good to very good inhibition, 100%=complete inhibition).

Compounds 1.007, 1.010, 1.014, 1.019, 1.020, 1.021, 1.023, 1.097, 1.098, 1.104, 1.106 and 1.107 show very good activity in this test ($\geq$80% inhibition).

Example B-2

Action Against *Mycosphaerella arachidis* (Early Leaf Spot of Groundnut; *Cercospora arachidicola* [fanamorph])—Fungal Growth Assay Conidia of the fungus from cryogenic storage were directly mixed into nutrient broth (PDB potato dextrose broth). After placing a (DMSO) solution of the test compounds (0.002% active ingredient) into a microtiter plate (96-well format) the nutrient broth containing the fungal spores was added. The test plates were incubated at 24° C. and the inhibition of growth was measured photometrically after 6-7 days. The activity of a compound was expressed as fungal growth inhibition (0=no growth inhibition, ratings of 80% to 99% mean good to very good inhibition, 100%=complete inhibition).

Compounds 1.003, 1.007, 1.010, 1.014, 1.016, 1.019, 1.020, 1.021, 1.023, 1.091, 1.092, 1.097, 1.098, 1.101, 1.103, 1.104, 1.105, 1.106 and 1.107 show very good activity in this test ($\geq$80% inhibition).

Example B-3

Action Against *Septoria tritici*—Fungal Growth Assay

Conidia of the fungus from cryogenic storage were directly mixed into nutrient broth (PDB potato dextrose broth). After placing a (DMSO) solution of the test compounds (0.002% active ingredient) into a microtiter plate (96-well format) the nutrient broth containing the fungal spores was added. The test plates were incubated at 24° C. and the inhibition of growth was determined photometrically after 72 hrs. The activity of a compound was expressed as fungal growth inhibition (0=no growth inhibition, ratings of 80% to 99% mean good to very good inhibition, 100%=complete inhibition).

Compounds 1.003, 1.010, 1.014, 1.019, 1.020, 1.021, 1.023, 1.091, 1.092, 1.097 and 1.098 show very good activity in this test ($\geq$80% inhibition).

Compounds 1.003, 1.007, 1.010, 1.014, 1.016, 1.019, 1.020, 1.021, 1.023, 1.091, 1.092, 1.097, 1.098, 1.101, 1.103, 1.104, 1.105, 1.106 and 1.107 show very good activity in this test ($\geq$80% inhibition).

Example B-4

Action Against *Monographella nivalis* (anamorph: *Fusarium nivale, Microdochium nivale*; Snow Mould)—Fungal Growth Assay Conidia of the fungus from cryogenic storage were directly mixed into nutrient broth (PDB potato dextrose broth). After placing a DMSO-solution of the test compounds (0.002% active ingredient) into a microtiter plate (96-well format) the nutrient broth containing the fungal spores was added. The test plates were incubated at 24° C. and the inhibition of growth was measured photometrically after 72 hrs (0=no growth inhibition, ratings of 80% to 99% mean good to very good inhibition, 100%=complete inhibition).

Compounds 1.007 and 1.023 show good activity in this test ($\geq$50% inhibition).

Example B-5

Action Against *Erysiphe graminis* f. sp. tritici (Wheat Powdery Mildew)

Wheat leaf segments were placed on agar in multiwell plates (24-well format) and sprayed with test solutions (0.02% active ingredient). After drying, the leaf disks were inoculated with a spore suspension of the fungus. After appropriate incubation the activity of a compound was assessed 7 days after inoculation as preventive fungicidal activity.

Compounds 1.003, 1.007, 1.010, 1.014, 1.016, 1.019, 1.021, 1.023, 1.098, 1.101 and 1.107 show very good activity in this test ($\geq$80% inhibition).

Example B-6

Protective Action Against *Puccinia recondita* (Brown Rust) on Wheat

Wheat leaf segments were placed on agar in multiwell plates (24-well format) and sprayed with test solutions (0.02% active ingredient). After drying, the leaf disks were inoculated with a spore suspension of the fungus. After appropriate incubation the activity of a compound was assessed 8 days after inoculation as preventive fungicidal activity.

Compounds 1.003, 1.007, 1.010, 1.014, 1.019, 1.020, 1.021, 1.091, 1.098, 1.103, 1.105, 1.106 and 1.107 show very good activity in this test ($\geq$80% inhibition).

Example B-7

Curative Action Against *Puccinia recondita* (Brown Rust) on Wheat

Wheat leaf segments were placed on agar in multiwell plates (24-well format) and inoculated with a spore suspension of the fungus. One day after inoculation the leaf segments were sprayed with test solutions (0.02% active ingredient). After appropriate incubation the activity of a compound was assessed 8 days after inoculation as curative fungicidal activity.

Compound 1.014, 1.016 and 1.106 show very good activity in this test ($\geq$80% inhibition).

Compound 1.091 and 1.107 show good activity in this test (50% inhibition).

Example B-8

Action Against *Pyrenophora teres* (Net Blotch) on Barley

Barley leaf segments were placed on agar in multiwell plates (24-well format) and sprayed with test solutions (0.02% active ingredient). After drying, the leaf disks were inoculated with a spore suspension of the fungus. After appropriate incubation the activity of a compound was assessed 4 days after inoculation as preventive fungicidal activity.

Compounds 1.003, 1.010, 1.014, 1.019, 1.020, 1.021, 1.023, 1.091, and 1.098 show very good activity in this test ($\geqq$80% inhibition).

Compounds 1.003, 1.007, 1.010, 1.014, 1.016, 1.019, 1.020, 1.021, 1.023, 1.091, 1.098, 1.104, 1.105, 1.106 and 1.107 show very good activity in this test ($\geqq$80% inhibition).

Comparative Biological Examples with the Structurally Closest Prior Art Compounds In the following biological tests, the fungicidal activity of compound No. 1.023 of this invention is compared with the fungicidal activity of compound No. 1.042 described on page 21 of WO 2009/024342.

(Compound No. 1.023 according to this invention)

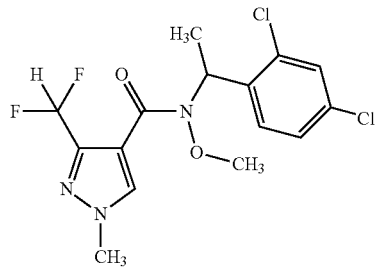

(Compound No. 1.042 according to prior art)

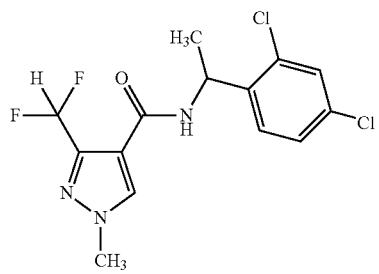

Except for the substitution pattern of the nitrogen atom of the amide, both structures are identical.

Example B-9

*Blumeria graminis* f. sp. *tritici* (*Erysiphe graminis* f. sp. tritici)/Wheat/Leaf Disc Preventive (Powdery mildew on wheat) Wheat leaf segments were placed on agar in a multiwell plate (24-well format) and sprayed with test solutions. After drying, the leaf disks were inoculated with a spore suspension of the fungus. After appropriate incubation the activity of a compound was assessed 4 dpi (days after inoculation) as preventive fungicidal activity.

| Compound | 200 ppm | 60 ppm | 20 ppm |
| --- | --- | --- | --- |
| No. 1.023 (this invention) | 100 | 100 | 90 |
| No. 1.042 (prior art) | 100 | 50 | 0 |

Example B-10

*Puccinia recondita*/Wheat/Leaf Disc Preventative (Brown Rust)

Wheat leaf segments were placed on agar in multiwell plates (24-well format) and sprayed with test solutions. After drying, the leaf disks were inoculated with a spore suspension of the fungus. After appropriate incubation the activity of a compound was assessed 8 dpi (days after inoculation) as preventive fungicidal activity.

| Compound | 200 ppm | 60 ppm | 20 ppm |
| --- | --- | --- | --- |
| No. 1.023 (this invention) | 70 | 50 | 0 |
| No. 1.042 (prior art) | 50 | 0 | 0 |

Example B-11

*Phaeosphaeria nodorum* (*Septoria nodorum*)/Wheat/Leaf Disc Preventative (Glume Blotch)

Wheat leaf segments were placed on agar in a multiwell plate (24-well format) and sprayed with test solutions. After drying, the leaf disks were inoculated with a spore suspension of the fungus. After appropriate incubation the activity of a compound was assessed 4 dpi (days after inoculation) as preventive fungicidal activity.

| Compound | 200 ppm | 60 ppm | 20 ppm |
| --- | --- | --- | --- |
| No. 1.023 (this invention) | 90 | 90 | 70 |
| No. 1.042 (prior art) | 70 | 0 | 0 |

Example B-12

*Pyrenophora teres*/Barley/Leaf Disc Preventive (Net Blotch)

Barley leaf segments were placed on agar in a multiwell plate (24-well format) and sprayed with test solutions. After drying, the leaf disks were inoculated with a spore suspension of the fungus. After appropriate incubation the activity of a compound was assessed 4 dpi (days after inoculation) as preventive fungicidal activity.

| Compound | 200 ppm | 60 ppm | 20 ppm |
|---|---|---|---|
| No. 1.023 (this invention) | 100 | 100 | 100 |
| No. 1.042 (prior art) | 100 | 90 | 50 |

Example B-13

*Alternaria solani*/Tomato/Leaf Disc (Early Blight)

Tomato leaf disks were placed on water agar in multiwell plates (24-well format) and sprayed with test solutions. After drying, the leaf disks were inoculated with a spore suspension of the fungus. After appropriate incubation the activity of a compound was assessed 4 dpi (days after inoculation) as preventive fungicidal activity.

| Compound | 200 ppm | 60 ppm | 20 ppm |
|---|---|---|---|
| No. 1.023 (this invention) | 100 | 100 | 90 |
| No. 1.042 (prior art) | 70 | 20 | 0 |

Example B-14

*Botryotinia fuckeliana* (*Botrytis cinerea*)/Liquid Culture (Gray Mould)

Conidia of the fungus from cryogenic storage were directly mixed into nutrient broth. After placing a (DMSO) solution of the test compounds into a microtiter plate (96-well format) the nutrient broth containing the fungal spores was added. The test plates were incubated at 24° C. and the inhibition of growth is determined photometrically after 3-4 days.

| Compound | 200 ppm | 60 ppm | 20 ppm |
|---|---|---|---|
| No. 1.023 (this invention) | 100 | 100 | 20 |
| No. 1.042 (prior art) | 50 | 20 | 0 |

Example B-15

*Mycosphaerella arachidis* (*Cercospora arachidicola*)/Liquid Culture (Early Leaf Spot)

Conidia of the fungus from cryogenic storage were directly mixed into nutrient broth (PDB potato dextrose broth). After placing a (DMSO) solution of the test compounds into a microtiter plate (96-well format) the nutrient broth containing the fungal spores was added. The test plates were incubated at 24° C. and the inhibition of growth is measured photometrically after 6-7 days.

| Compound | 60 ppm | 20 ppm | 6 ppm |
|---|---|---|---|
| No. 1.023 (this invention) | 100 | 100 | 100 |
| No. 1.042 (prior art) | 100 | 100 | 0 |

Example B-16

*Mycosphaerella praminicola* (*Seotoria tritici*)/Liquid Culture (Septoria Blotch)

Conidia of the fungus from cryogenic storage were directly mixed into nutrient broth (PDB potato dextrose broth). After placing a (DMSO) solution of the test compounds into a microtiter plate (96-well format) the nutrient broth containing the fungal spores was added. The test plates were incubated at 24° C. and the inhibition of growth is measured photometrically after 4 days.

| Compound | 60 ppm | 20 ppm | 6 ppm |
|---|---|---|---|
| No. 1.023 (this invention) | 100 | 100 | 100 |
| No. 1.042 (prior art) | 100 | 100 | 20 |

Example B-17

*Gaeumannomyces graminis*/Liquid Culture (Take-All of Cereals)

Mycelial fragments of the fungus from cryogenic storage were directly mixed into nutrient broth (PDB potato dextrose broth). After placing a (DMSO) solution of the test compounds into a microtiter plate (96-well format) the nutrient broth containing the fungal spores was added. The test plates were incubated at 24 C and the inhibition of growth was determined photometrically after 2-3 days.

| Compound | 60 ppm | 20 ppm | 6 ppm |
|---|---|---|---|
| No. 1.023 (this invention) | 50 | 0 | 0 |
| No. 1.042 (prior art) | 0 | 0 | 0 |

Example B-18

*Monopraphella nivalis* (*Microdochium nivale*)/Liquid Culture (Foot Rot Cereals Conidia of the fungus from cryogenic storage were directly mixed into nutrient broth (PDB potato dextrose broth). After placing a (DMSO) solution of the test compounds into a microtiter plate (96-well format) the nutrient broth containing the fungal spores was added. The test plates were incubated at 24° C. and the inhibition of growth is measured photometrically after 4-6 days.

| Compound | 60 ppm | 20 ppm | 6 ppm |
|---|---|---|---|
| No. 1.023 (this invention) | 50 | 0 | 0 |
| No. 1.042 (prior art) | 50 | 0 | 0 |

From the above results in Examples B-9 to B-18 can be derived that the fungicidal activity of the compound No. 1.023 according to the invention is in general clearly superior to the activity of the prior art compound No. 1.042 at low application rates for the listed plant diseases under the described test conditions. This superior performance is important because it allows a more efficient disease control of tested plant diseases at significantly lower application rates. In the light of the structural similarities of the tested compounds, this surprising improvement of the fungicidal properties is completely unexpected and cannot be derived from what is known from the prior art.

What is claimed is:

1. A compound of formula I

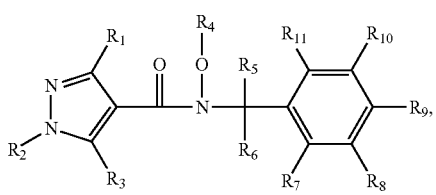

wherein
$R_1$ is $C_1$-$C_4$alkyl or $C_1$-$C_4$haloalkyl;
$R_2$ is $C_1$-$C_4$alkyl;
$R_3$ is hydrogen or halogen;
$R_4$ is hydrogen, $C_1$-$C_4$alkyl or $C_1$-$C_4$halogenalkyl;
$R_5$ and $R_6$ are, independently from each other, hydrogen, halogen, $C_1$-$C_4$alkyl or $C_1$-$C_4$haloalkyl;
$R_8$ and $R_{10}$ are, independently from each other, hydrogen, halogen, $C_1$-$C_6$alkyl, phenyl which can be mono- or di-substituted by halogen or phenoxy which can be mono- or di-substituted by halogen;
or $R_7$ and $R_8$ together or $R_8$ and $R_9$ together form together with the carbon atoms to which they are attached, a six-membered aromatic ring; and
$R_7$, $R_9$ and $R_{11}$ are, independently from each other, hydrogen, hydroxy, halogen, $C_1$-$C_6$alkyl, $C_3$-$C_6$alkinyl, $C_1$-$C_4$alkoxy, halophenoxy, $C_1$-$C_6$haloalkyl or $C_1$-$C_6$haloalkoxy;
and agronomically acceptable salts/il/stereoisomers/diastereoisomers/enantiomers/tautomers and N-oxides of those compounds.

2. A compound according to claim 1, wherein
$R_1$ is $C_1$-$C_4$haloalkyl;
$R_2$ is $C_1$-$C_4$ alkyl;
$R_3$ is hydrogen;
$R_4$ is $C_1$-$C_4$alkyl;
$R_5$ is hydrogen or $C_1$-$C_4$alkyl;
$R_6$ is hydrogen;
$R_7$ is hydrogen, $C_1$-$C_4$alkoxy or halogen;
$R_8$ is hydrogen, halogen, phenyl which can be mono- or di-substituted by halogen or phenoxy which can be mono- or di-substituted by halogen;
or $R_7$ and $R_8$ together or $R_8$ and $R_9$ together form together with the carbon atoms to which they are attached, a six-membered aromatic ring;
$R_9$ is hydrogen, halogen or phenoxy which can be substituted by halogen;
$R_{10}$ is hydrogen and
$R_{11}$ is hydrogen.

3. A compound according to claim 2, wherein $R_5$ is methyl.

4. A compound according to claim 1, wherein
$R_1$ is difluoromethyl;
$R_2$ is methyl;
$R_3$ is hydrogen;
$R_4$ is methyl;
$R_5$ is hydrogen or methyl;
$R_6$ is hydrogen;
$R_7$ is hydrogen, methoxy or chloro;
$R_8$ is hydrogen; iodine, phenyl is mono- or di-substituted by chlorine or phenoxy which is mono- or di-substituted by chlorine;
or $R_7$ and $R_8$ together or $R_8$ and $R_9$ together form together with the carbon atoms to which they are attached, a six-membered aromatic ring;
$R_9$ is hydrogen, iodine, chlorine or phenoxy which is substituted by chlorine;
$R_{10}$ is hydrogen and
$R_{11}$ is hydrogen.

5. A compound according to claim 1, wherein
$R_1$ is difluoromethyl, trifluoromethyl or methyl,
$R_2$ is methyl;
$R_3$ is hydrogen or fluoro;
$R_4$ is hydrogen, methyl or ethyl; preferably methyl;
$R_5$ is hydrogen, methyl or ethyl; and
$R_6$ is hydrogen.

6. A compound according to claim 1, wherein
$R_1$ is difluoromethyl or trifluoromethyl;
$R_2$ is methyl;
$R_3$ is hydrogen;
$R_4$ is methyl;
$R_5$ is hydrogen, methyl or ethyl;
$R_6$ is hydrogen;
$R_8$ is hydrogen; iodine, phenyl which can be mono- or di-substituted by chlorine, phenoxy which can be mono- or di-substituted by chlorine, phenyl which can be mono- or di-substituted by chlorine,
$R_{10}$ is hydrogen;
$R_7$, $R_9$ and $R_{11}$ are, independently from each other, hydrogen or halogen, preferably hydrogen or chlorine.

7. A method of controlling infestation of useful plants by phytopathogenic microorganisms, wherein a compound of formula I according to claim 1 or a composition, comprising this compound as active ingredient, is applied to the plants, to parts thereof or the locus thereof.

8. A composition for controlling phytopathogenic microorganisms, comprising a compound of formula I according to claim 1 and at least one inert carrier.

* * * * *